US009327516B2

(12) United States Patent
Britz

(10) Patent No.: US 9,327,516 B2
(45) Date of Patent: May 3, 2016

(54) HISTOLOGICAL SPECIMEN CASSETTE

(75) Inventor: Todd A. Britz, Maple Grove, MN (US)

(73) Assignee: Primera Technology, Inc., Minneapolis, MN (US)

( * ) Notice: Subject to any disclaimer, the term of this patent is extended or adjusted under 35 U.S.C. 154(b) by 253 days.

(21) Appl. No.: 13/822,552

(22) PCT Filed: Aug. 25, 2011

(86) PCT No.: PCT/US2011/049221
§ 371 (c)(1),
(2), (4) Date: May 9, 2013

(87) PCT Pub. No.: WO2012/036867
PCT Pub. Date: Mar. 22, 2012

(65) Prior Publication Data
US 2013/0224088 A1    Aug. 29, 2013

Related U.S. Application Data

(60) Provisional application No. 61/382,193, filed on Sep. 13, 2010, provisional application No. 61/387,557, filed on Sep. 29, 2010, provisional application No. 61/433,595, filed on Jan. 18, 2011.

(51) Int. Cl.
*A61B 10/00* (2006.01)
*B41J 3/407* (2006.01)
(Continued)

(52) U.S. Cl.
CPC ............... *B41J 3/407* (2013.01); *B01L 3/5055* (2013.01); *B41J 2/325* (2013.01); *G01N 35/1002* (2013.01); *G01N 1/312* (2013.01)

(58) Field of Classification Search
CPC .................................. G01N 1/36; B01L 3/5055
See application file for complete search history.

(56) References Cited

U.S. PATENT DOCUMENTS 2,707,066 A    4/1955   Stegeman 4,171,131 A    10/1979   Stange et al.
(Continued)

FOREIGN PATENT DOCUMENTS

DE      3713077 A1    10/1987
JP       58162442 A     9/1983
(Continued)

OTHER PUBLICATIONS

International Search Report and Written Opinion issued in PCT/US2011/049221, mailed Mar. 19, 2012, 9 pages.
(Continued)

*Primary Examiner* — Jyoti Nagpaul
(74) *Attorney, Agent, or Firm* — Faegre Baker Daniels LLP

(57) ABSTRACT

A unitary molded polymer histological specimen cassette includes a base defining a compartment, a lid, and a hinge connecting the lid to the base and enabling the lid to move between an open position and a closed position with respect to the base. The lid and base are configured to form a fulcrum and apply sufficient tension to the hinge to fracture the hinge when the lid is moved from the open position to the closed position. Another embodiment of the cassette includes a panel extending from the base and having a print-receptive front surface, a rear surface and a first thickness. A plurality of spaced apart support walls extend between and are integrally molded with the base and the rear surface of the panel to support the panel with respect to the base. The cassette includes a sufficient number of support walls at spaced-apart positions to provide the panel with sufficient rigidity to enable printing on the print-receptive surface. All of the support walls have a substantially equal second thickness that is less than the first thickness of the panel, and the second thickness is a thickness with respect to the first thickness that causes the panel to be sufficiently flat and smooth to enable printing on the print-receptive surface.

21 Claims, 33 Drawing Sheets

(51) Int. Cl.
*G01N 35/10* (2006.01)
*B41J 2/325* (2006.01)
*B01L 3/00* (2006.01)
*G01N 1/31* (2006.01)

(56) References Cited

U.S. PATENT DOCUMENTS

| | | | |
|---|---|---|---|
| 4,220,252 | A | 9/1980 | Beall et al. |
| 4,705,414 | A | 11/1987 | Guy et al. |
| 4,823,535 | A | 4/1989 | Schmidt et al. |
| 4,997,100 | A | 3/1991 | Dudek |
| 5,167,407 | A | 12/1992 | Namba |
| 5,267,800 | A | 12/1993 | Petteruti et al. |
| 5,365,312 | A | 11/1994 | Hillmann et al. |
| 5,372,439 | A | 12/1994 | Poole et al. |
| 5,423,619 | A | 6/1995 | Kohno |
| 5,538,688 | A | 7/1996 | Tezuka et al. |
| 5,562,402 | A | 10/1996 | Muto |
| 5,676,910 | A | 10/1997 | Levine et al. |
| 5,683,786 | A | 11/1997 | Kavanaugh |
| 5,948,685 | A | 9/1999 | Angros |
| 5,963,368 | A | 10/1999 | Domanik et al. |
| 6,164,757 | A | 12/2000 | Wen et al. |
| 6,228,805 | B1 | 5/2001 | Ohshima et al. |
| 6,261,012 | B1 | 7/2001 | Haas et al. |
| 6,395,554 | B1 | 5/2002 | Regan et al. |
| 6,615,763 | B2 | 9/2003 | Edwards |
| 6,629,792 | B1 | 10/2003 | Geddes et al. |
| 6,715,870 | B2 | 4/2004 | Kiene et al. |
| 6,899,030 | B2 | 5/2005 | Fowlkes et al. |
| 6,951,663 | B1 | 10/2005 | Edwards |
| 7,124,681 | B2 | 10/2006 | Louviere et al. |
| 7,271,008 | B2 | 9/2007 | Floyd |
| 7,449,147 | B2 | 11/2008 | Metzner et al. |
| 7,556,779 | B2 | 7/2009 | Melching et al. |
| 7,578,150 | B2 * | 8/2009 | Zsambeki .............. 68/17 R |
| 7,579,190 | B2 | 8/2009 | Ostgaard et al. |
| 7,637,713 | B1 | 12/2009 | Parette |
| 7,833,485 | B2 | 11/2010 | Higuchi et al. |
| 8,013,884 | B2 | 9/2011 | Schlinkmann et al. |
| 2001/0039896 | A1 | 11/2001 | Edwards |
| 2002/0167577 | A1 | 11/2002 | Kiene et al. |
| 2003/0049178 | A1 | 3/2003 | Kiene et al. |
| 2003/0059281 | A1 | 3/2003 | Kiene et al. |
| 2003/0092186 | A1 | 5/2003 | Pressman et al. |
| 2004/0166030 | A1 | 8/2004 | Lafond et al. |
| 2005/0094263 | A1 | 5/2005 | Vaccarelli |
| 2005/0219344 | A1 | 10/2005 | Bouchard et al. |
| 2006/0051241 | A1 | 3/2006 | Higuchi et al. |
| 2006/0113315 | A1 | 6/2006 | Chen |
| 2006/0216099 | A1 | 9/2006 | Sakano et al. |
| 2007/0140920 | A1 | 6/2007 | McCormick |
| 2007/0141711 | A1 | 6/2007 | Stephens et al. |
| 2007/0240587 | A1 | 10/2007 | Fengler |
| 2008/0138854 | A1 * | 6/2008 | Williamson .............. 435/40.52 |
| 2009/0223390 | A1 | 9/2009 | Schlinkmann et al. |
| 2009/0270765 | A1 | 10/2009 | Ghesquiere et al. |
| 2010/0005088 | A1 | 1/2010 | Zhang |
| 2010/0075410 | A1 | 3/2010 | Desai et al. |
| 2010/0184127 | A1 | 7/2010 | Williamson, IV et al. |
| 2010/0220162 | A1 | 9/2010 | Schierholz et al. |
| 2013/0220156 | A1 | 8/2013 | Haas et al. |
| 2013/0222444 | A1 | 8/2013 | Cummins et al. |
| 2014/0078235 | A1 | 3/2014 | Cummins et al. |
| 2014/0212256 | A1 | 7/2014 | Haas |
| 2014/0225947 | A1 | 8/2014 | Cummins et al. |

FOREIGN PATENT DOCUMENTS

| | | | |
|---|---|---|---|
| JP | 60055264 | A | 3/1985 |
| JP | 62030962 | A | 2/1987 |
| JP | 2003312063 | A | 11/2003 |
| KR | 100397256 | B1 | 10/1996 |
| WO | WO2009114471 | A1 | 9/2009 |
| WO | WO2010032045 | A1 | 3/2010 |
| WO | WO2012004596 | A9 | 1/2012 |
| WO | WO2012036865 | A2 | 3/2012 |
| WO | WO2012036866 | A2 | 3/2012 |
| WO | WO2012036867 | A2 | 3/2012 |
| WO | WO2012036874 | A2 | 3/2012 |

OTHER PUBLICATIONS

PPM-21 Maintenance Manual, Takefuji Chemical Co., Ltd., Apr. 10, 2002, 63 pgs. (Japanese document and English translation).

PPM-21 Operation Manual, First Edition: Oct. 14, 2003, Second Edition: Feb. 9, 2005, 55 pgs. (Japanese document and English translation).

PPM-21 Specifications, No. 209A203A, Jul. 3, 2002, 25 pgs. (Japanese document and English translation).

"Sakura Super Frost Printer SSP-600", Sakura Seiki, Jan. 3, 1989, 7 pp.

"Tissue-Tek® AutoWrite Printers—Slide and Cassette Printers", Sakura Finetek USA, Inc., 2003, 4 pp.

[JP document and English translation]Sakura Super Frost II [online], [retrieved 2004] Retrievd from Internet Archive Wayback Machine searching Matsunami Glass website using Internet <URL:http://www.web.archive.org/web/20040414050043/http://www.matsunami-glass.co.jp/e-index.html>.

Color ID Card Printer Operating Instructions, Copyright 1997, 78 pp.

Color ID Card Printer Technical Service and Maintenance Manual, Copyright 1994, 52 pp.

International Preliminary Report on Patentability, Chapter II, issued in PCT/US2011/049214, mailed Jan. 3, 2013, 4 pages.

International Preliminary Report on Patentability, Chapter II, issued in PCT/US2011/049221, mailed Dec. 17, 2012, 5 pages.

International Search Report and Written Opinion issued in PCT/US2011/049214, mailed Apr. 10, 2012, 8 pages.

International Search Report and Written Opinion issued in PCT/US2011/049218, mailed Apr. 23, 2012, 9 pages.

International Search Report and Written Opinion issued in PCT/US2011/049380, mailed Mar. 26, 2012, 11 pages.

Internet Archive Wayback Machine, TBS—Triangle Biomedical Sciences, Retrieved from the Internet at http://web.archive.org/web/20021206191110/http://trianglebiomedical.com/prodShurMark on Feburary 3, 2014. 2 pgs.

Shandon Microwriter™ Labeler Series, Complete laboratory labeling solutions, Thermo Electron Corporation, Sep. 2003., 8 pgs.

Shandon Microwriter™ Labeler Series, Thermo Electron Corporation, Aug. 2005, 20 pgs.

SHUR/Mark® PLUS, Innovative Slide and Cassette Labeling Instrumentation/Software Operations and Service Manual, Version 5.0, TBS—Triangle Biomedical Sciences, Inc., Jan. 2001, 104 pgs.

SHUR/Mark® PLUS, Innovative Slide and Cassette Labeling Technology, TBS—Triangle Biomedical Sciences, Inc., Apr. 2004, 2 pgs.

Supplementary European Search Report issued in EP Application No. 11825648, completed Feb. 21, 2014, 8 pages.

Tissue-Tek® Autowrite™ Slide Printer Operating Manual, Sakura Finetek USA, Inc., Aug. 12, 2003, 66 pgs.

Tissue-Tek® Autowrite™ Software Instructions, Sakura Finetek USA, Inc., 2007, 40 pgs.

* cited by examiner

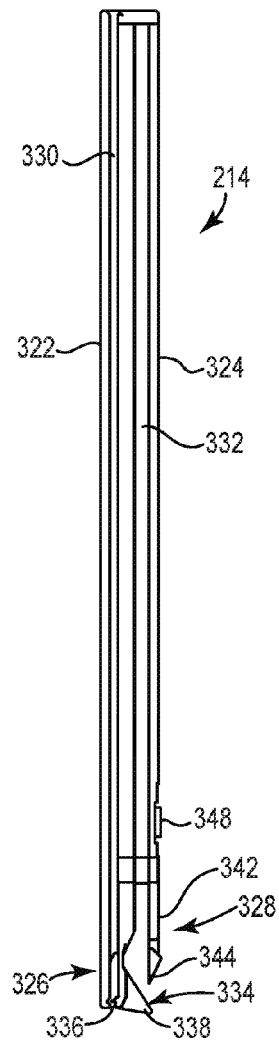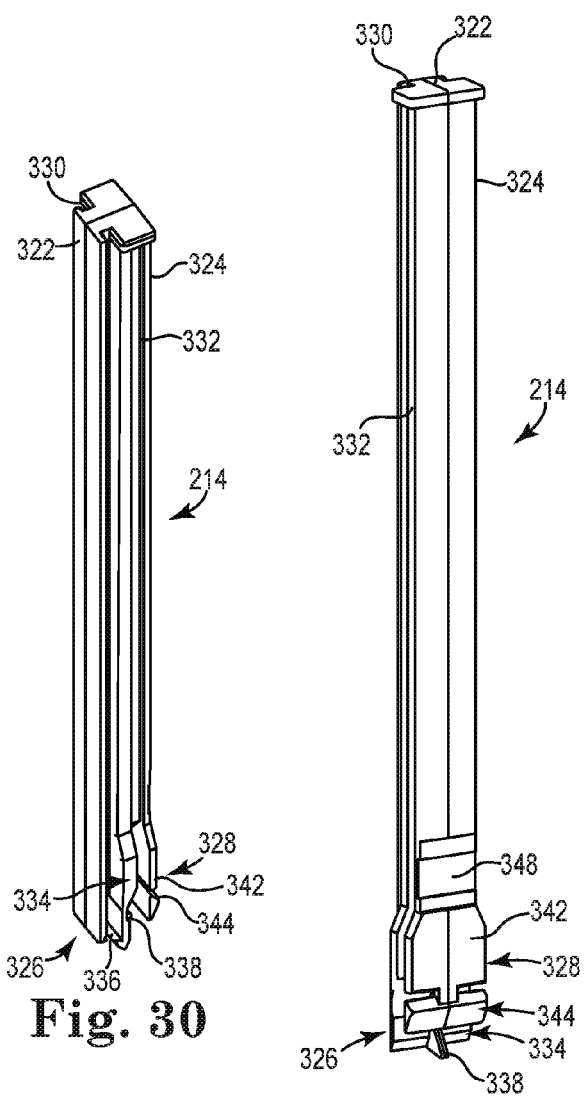
Fig. 29　Fig. 30　Fig. 31

HISTOLOGICAL SPECIMEN CASSETTE

BACKGROUND

The present invention relates to histological specimen cassettes.

Cassettes used to process histological specimens (e.g., tissue biopsies) are generally known and commercially available. One common form of cassette includes a base defining a compartment for the specimen, a lid connected to the base by a hinge, and a panel extending from a front wall of the base. Specimen information can be printed on the panel in the form of a bar code and/or text. There remains, however, a continuing need for improved specimen cassettes. In particular, there is a need for cassettes that are efficient to manufacture and use while enabling accurate specimen processing.

SUMMARY

The invention is a histological specimen cassette that is efficient to manufacture and use, and enables accurate tissue processing. For example, the panel is configured to enable specimen information to be accurately and reliably printed thereon by thermal and other printers. The hinge connecting the lid to the base automatically and reliably ruptures or breaks to separate the lid from the base when it is initially closed, but can be easily reopened and reclosed.

One embodiment of the invention is a histological specimen cassette. The cassette comprises a base defining a compartment, a lid, and a hinge connecting the lid to the base and enabling the lid to move between an open position and a closed position with respect to the base. The lid and base are configured to form a fulcrum and apply sufficient tension to the hinge to fracture the hinge when the lid is moved from the open position to the closed position. In some embodiments the base, lid and hinge are unitary molded polymer elements. In other embodiments the hinge has a length, the locations that the hinge connects to the base and the lid are separated by a first distance when the lid is in the closed position, and the length of the hinge is less than the first distance.

Another embodiment of the invention is a unitary molded polymer histological specimen cassette comprising a base defining a compartment, a panel extending from the base and having a print-receptive front surface, a rear surface and a first thickness, and a plurality of spaced apart support walls extending between and integrally molded with the base and the rear surface of the panel to support the panel with respect to the base. The plurality of support walls includes a sufficient number of support walls at spaced-apart positions to provide the panel with sufficient rigidity to enable printing on the print-receptive surface, and all of the plurality of support walls have a substantially equal second thickness that is less than the first thickness of the panel and wherein the second thickness is a thickness with respect to the first thickness that causes the panel to be sufficiently flat and smooth to enable printing on the print-receptive surface.

Yet another embodiment of the invention is a unitary molded polymer histological specimen cassette comprising a base defining a compartment and a lid. The base includes a bottom wall, a front end wall, a pair of side walls, and a rear end wall having an upper edge and a flange extending in a direction opposite the compartment. The lid is movable between open and closed positions with respect to the base and includes a rear end portion and a flange that extends from the rear end portion. The flange of the lid and the flange of the base rear end wall are separated by a first distance when the lid is in the closed position. A hinge connects the flange of the lid to the flange of the base rear end wall. The hinge has a length that is less than the first distance and enables the lid to move between the open and closed positions. An underside surface of the lid engages the upper edge of the base rear end wall and cooperate as a fulcrum to apply sufficient tension to the hinge to fracture the hinge when the lid is moved from the open position to the closed position. A panel having an edge is connected to the front end wall of the base and extends at an angle from the front end wall of the base. The panel has a print-receptive front surface, a rear surface and a first thickness. A plurality of substantially equal thickness, spaced apart support walls extend between the front end wall of the base and the rear surface of the panel. The support walls have a second thickness that is less than the first thickness. The plurality of support walls includes a sufficient number of support walls at spaced-apart positions to provide the panel with sufficient rigidity to enable printing on the print-receptive surface, and the second thickness of the support walls is a thickness with respect to the first thickness of the panel that causes the print-receptive surface of the panel to be sufficiently flat and smooth to enable printing on the print-receptive surface when the print-receptive surface is free from post-molding finishing.

BRIEF DESCRIPTION OF THE DRAWINGS

FIG. 29 is a side plan view of the cassette loading rod shown in FIG. 20.

FIG. 30 is an isometric view of the loading rod shown in FIG. 29, showing the front side.

FIG. 31 is an isometric view of the loading rod shown in FIG. 29, showing the back side.

DETAILED DESCRIPTION

Overview

Figure 53:
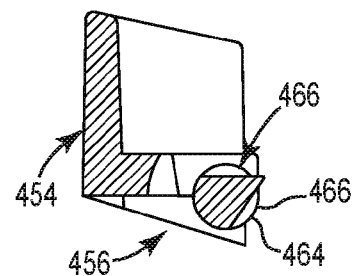
FIG. 53 is a sectional view of the output tray stop, taken along line 53-53 in FIG. 52.
Figure 52:
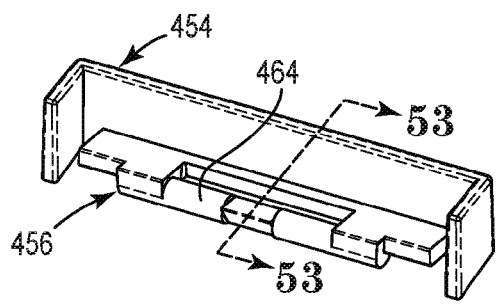
FIG. 52 is an isometric view of the stop of the output tray shown in FIGS. 45-47.

Color histological specimen container printers in accordance with the invention are described below in connection with FIGS. 1-53. One embodiment of the printer invention is a color slide printer 10 described in connection with FIGS. 1-9. Slide 100, a specimen container in accordance with one embodiment of the invention that can, for example, be color printed using the slide printer 10, is described in connection with FIG. 3. Another embodiment of the invention is a color cassette printer 200 described in connection with FIGS. 20-53. Cassette 500, a specimen container in accordance with the invention that can, for example, be color printed using the cassette printer 200, is described in connection with FIGS. 10-14. Yet another embodiment of a specimen container in accordance with the invention, cassette 600, can also be color printed using the cassette printer 200 and is described in connection with FIGS. 15-19.

Color Slide Printer 10

A color slide printing system 10 in accordance with one embodiment of the invention can be described generally with reference to FIGS. 1-5. As shown, slide printing system 10 includes an outer cabinet 12 in which components are mounted, and the cabinet includes a cross support wall 14 extending between and suitably supported on side walls 16. The side walls 16 are used for rotatably supporting various drive rollers and other components. A medical slide cartridge indicated generally at 18 (also sometimes referred to as a cassette or magazine) is a rectangular container that holds a plurality of individual slides 100. The slides 100 can be of a desired type, and can be clear or opaque and they will have a finish on at least portions of one surface that will accept ink from a thermal printer that has a multi-colored ribbon. A frosted finish in the area to be printed is suitable.

The cartridge 18 is a self-contained unit that can be loaded with slides 100 from the bottom or can have a suitable access cover, and it can be slid in and out of the outer printer housing 12 through a provided opening, and between side guides (FIG. 1) and rested on the support wall 14. As can be seen, the cartridge size is selected to support a number of slides 100 in a stack (usually 100), and the bottom wall 22 of the cartridge 18 has a feed opening 24 defined therein formed, by terminating the bottom wall 22 so it is spaced from an inner or infeed end wall 25. The end wall 25 is terminated with a bottom edge 26 spaced slightly above the top plane of the bottom wall 22, so that when a cartridge 18 is positioned in the print housing, as shown in FIG. 2, an input feed roller 28 will support the bottommost slide 100 (the roller 28 projects above wall 14), and hold the end of the slide position so that the bottom slide will clear the bottom edge 26. The input feed roller 28 will withdraw the bottom slide 100 through the opening 24 when the feed roller is powered.

The input feed roller 28 is driven by a suitable motor 32 from a central control system 34 which comprises a microcontroller that can be programmed for sequencing the various components being controlled in a desired manner and which coordinates the printing on the slide 100 for identification.

Provided slide guides 35 will support a slide 100 after it is moved by the input feed roller 28 underneath the wall edge 26, and the input feed roller 28 will provide an impetus to move the slide along the guides 35 until it is grasped by drive rollers indicated at 38 and 40. At least one of the drive rollers, for example drive roller 40 is driven by a motor 42 that is also controlled by the control system 34. The slide 100 being fed is grasped between the drive rollers 38 and 40 and is moved across a slide position sensor 37 onto a printer printhead platen roller 46 that is driven by a motor 48 from control system 34. The slide position sensor 37 provides a position signal to control system 34 so the drive rollers 38 and 40 are driven to properly position the slide 100 relative to the printhead.

Figure 5:
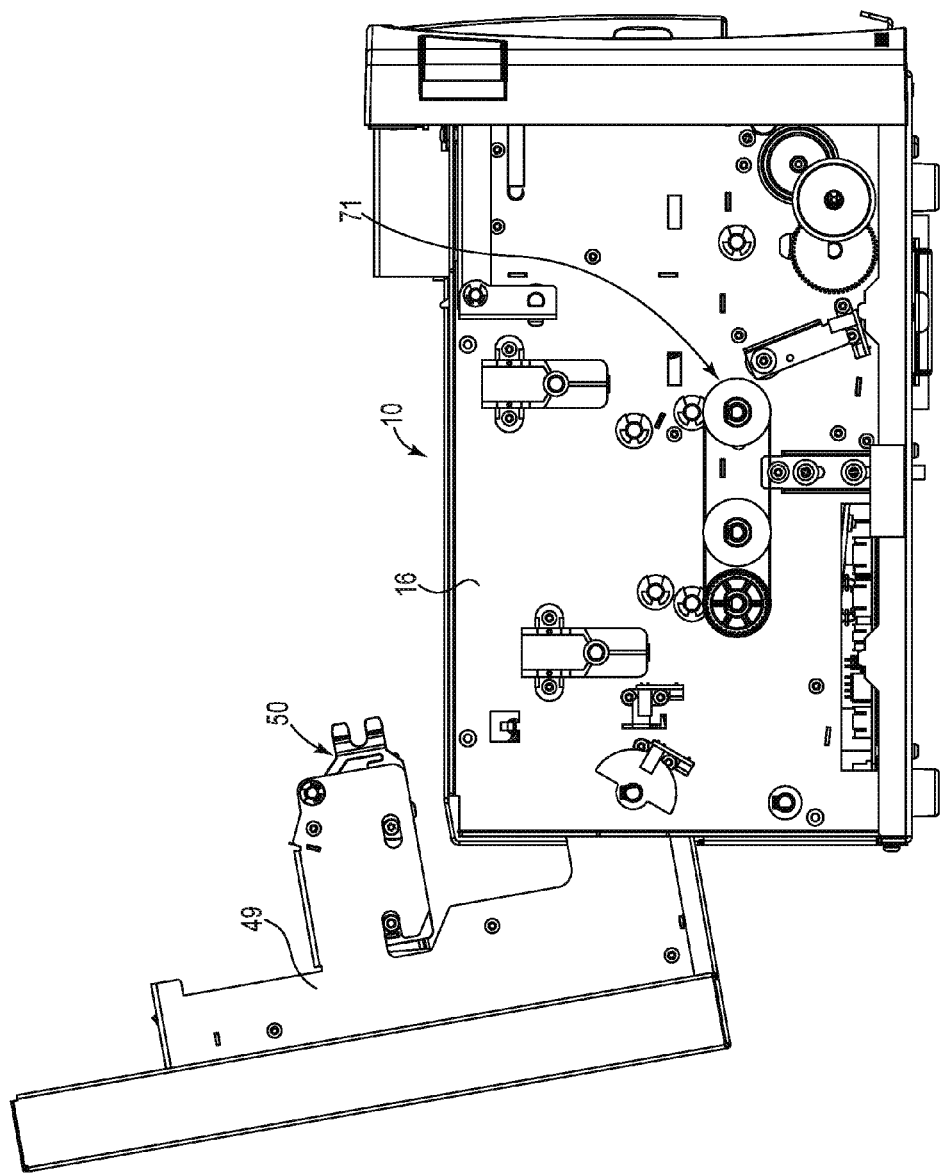
FIG. 5 is a side view of the printing system shown in FIG. 1, with a cover carrying the printer in an open position.

Printhead platen roller 46 is independently mounted between the side walls 16 of the housing, and above the platen roller there is a thermal printer indicated at 50 that includes a thermal printhead 52 that will print on an upper surface of a slide, for example, the slide 100A shown in FIG. 2 between the drive rollers 70 and 72 and supported on the printhead platen roller 46. The printer 50 is carried on a cover 49 that can be opened as shown in FIG. 5, and the printer is supported on the cover 49 for movement toward and away from printhead platen roller 46 when the cover 49 is closed. A lever 51 is pivoted at a pivot 51A and has an end finger 51B that engages a crossbar on the printer 50 frame. A cam 53 is positioned to act on a cam follower 51C on the lever 51 to lift the printer and printhead when the cam is rotated by a motor 55. The motor 55 is controlled by control system 34.

The slide 100A is moved beneath a multi-color thermal print ribbon indicated at 54 which is fed from a ribbon supply roller 56 mounted between the side walls 16 and which passes under the printhead 52. The print ribbon supply roller is driven by a suitable motor 59. The ribbon 54 is a known ribbon with blocks of heat transferable color along its length in a known sequence, namely yellow (Y), magenta (M), cyan (C) and black (K). The ribbon 54 passes across a print ribbon sensor 58 that provides signals indicating the start of each block of color on the ribbon to the control system 34. Guide rollers 57 are also provided for the ribbon 54 between the supply roller 56 and the printhead 52. The ribbon 54, after it has been used for printing onto the slide 100A, is taken up on a print ribbon take up roller 62, that can be driven with a suitable motor 64 controlled by the control system 34.

Prior to printing, the printhead 52 is raised by operating cam 53 to lift the printer and the slide 100A will be moved forwardly toward a pair of drive rollers 70 and 72 again, at least one of which is driven, for example by schematically illustrated motor 74 coordinated with the control system 34. It should be noted that while individual drive motors for the feed rollers and platen roller are shown for illustration purposes, the rollers that are timed or coordinated can be driven by one motor and a gear train shown generally at 71 in FIG. 5.

Figure 1:
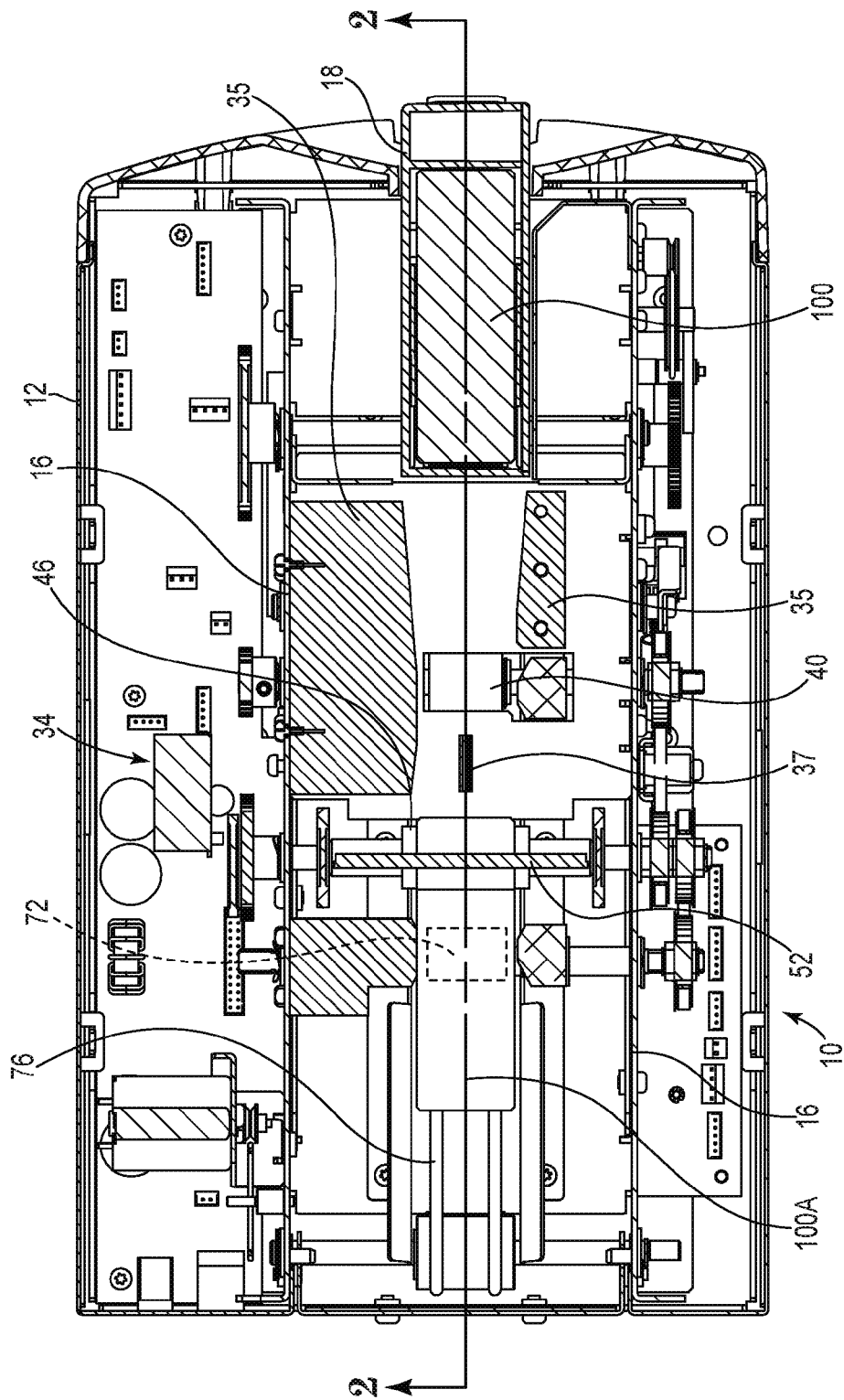
FIG. 1 is a top sectional view of a histological specimen slide printing system in accordance with one embodiment of the invention, taken on line 1-1 in FIG. 2
Figure 2:
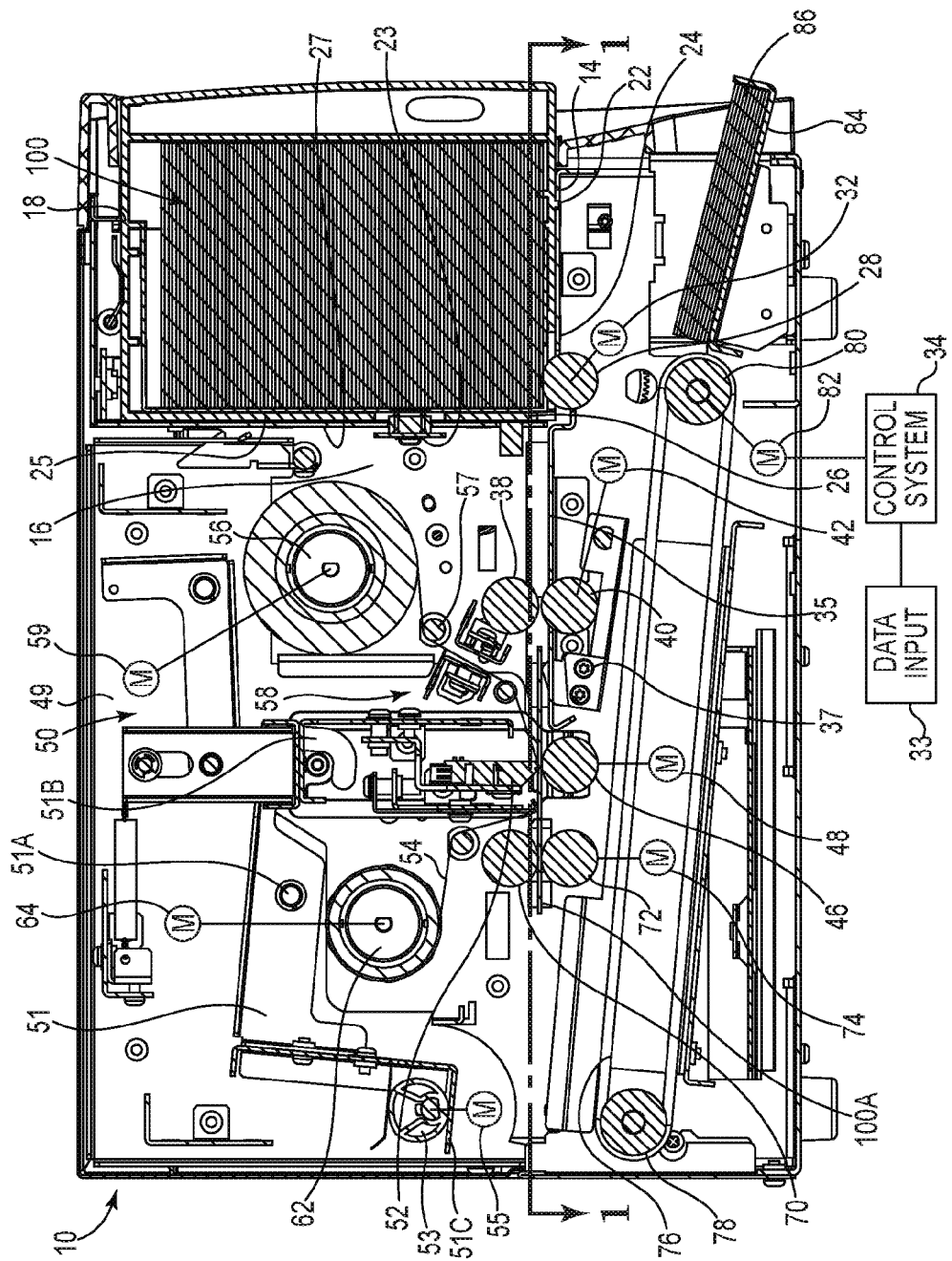
FIG. 2 is a sectional view of the slide printing system shown in FIG. 1, taken on line 2-2 in FIG. 1.
Figure 3:
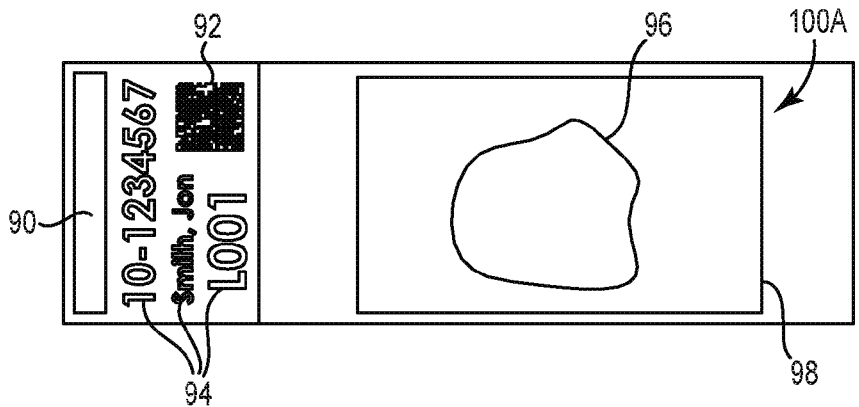
FIG. 3 is a top plan view of a slide printed in accordance with one embodiment of the invention by the printing system shown in FIG. 1.

As the slide 100A is printed (as shown in FIG. 1), it should be understood that it will be moved back and forth by drive rollers 70 and 72 and platen roller 46 under control of the control system 34. Printing occurs adjacent one end of the slide as shown in FIG. 3 so the drive rollers 70 and 72 are usable for moving the slide 100A while it is being printed on. The printhead 52 has enough lateral width so that the printing can take place along the lateral width of the slide wide enough to include the information necessary. The printhead 52 is lifted when needed for moving the slide 100A to reposition it.

After the slide 100A has been printed by printing a colored bar 90 (See FIG. 3), a bar code 92 and identification text 94, the slide is driven through the drive rollers 70 and 72 under the power of motor 74, and it is dropped into a storage facility. In this form, the printed slide is dropped onto a conveyor belt 76 that is mounted over first and second end rollers 78 and 80. The end of the conveyor supported by roller 80 is located back underneath the slide cartridge 18. The roller 80 can be driven by a suitable motor 82 controlled by the control system 34, or can be driven by the gear train 71.

The printed slides carried on the upper length of the conveyor belt 76 will be dropped into a slide output tray or bin 84 that is mounted in a suitable manner at an incline underneath the slide holder cartridge 18. The slides that have been printed have been shown at 86 in a stack.

The cartridges 18 could be loaded with different types of slides if desired, for example, if a party wanted to use colored slides with a monochrome ribbon instead of color ribbon with white or clear slides, the slide cartridge allows the user to easily switch slide colors without handling the slides. Multiple cartridges could be used to store multiple colors, which can be easily identified and switched while keeping them dust and fingerprint free.

In use, the administrator of the company that was using the slide identification system of the present disclosure would set up some variables for their system, for example, an automated color selection where a particular color identifies a particular tissue. For example, liver tissue could be blue; kidney tissue could be green; heart tissue could be red; lung tissue could be black and so on. The data input 33 into the software of the control system 34 can be manually input or read from another source, and used to identify the type of slide that was to be printed, and also for each particular slide the data would include in the software the text that was to be printed and the identification bar code that is to be printed on the slide. Then, the software would automatically select the slide identification color, based on the input data and the printhead would be operated to print the strip or identifying block 90 on the one end portion of the slide such as that shown in FIG. 3, and then the data relating to the specimen that would be placed on the slide is printed as text 94 and bar code 92 for identification. This can be done in a black color, so the slide information would be in two colors.

The thermal printer permits the color identifier bar or block 90 to be printed easily in a selected color and then the information about the tissue sample on the slide can be printed in a different color, such as black.

The ability to print the identifying color for the type of tissue that would be placed on the slide at the same time that the bar code is placed on eliminates errors in identifying the color code to be used.

FIG. 3 illustrates a typical slide 100A after printing and mounting a specimen thereon having the identifying color bar 90 shown in one portion of the slide and the printed data 94, including a bar code 92 that is printed in black and adjacent to the color bar and with a specimen 96 that is keyed to the information on the slide mounted on the slide. The specimen 96 can be covered by a slip cover 98 and retained on the slide in a known manner where desired.

Figures 6, 7:
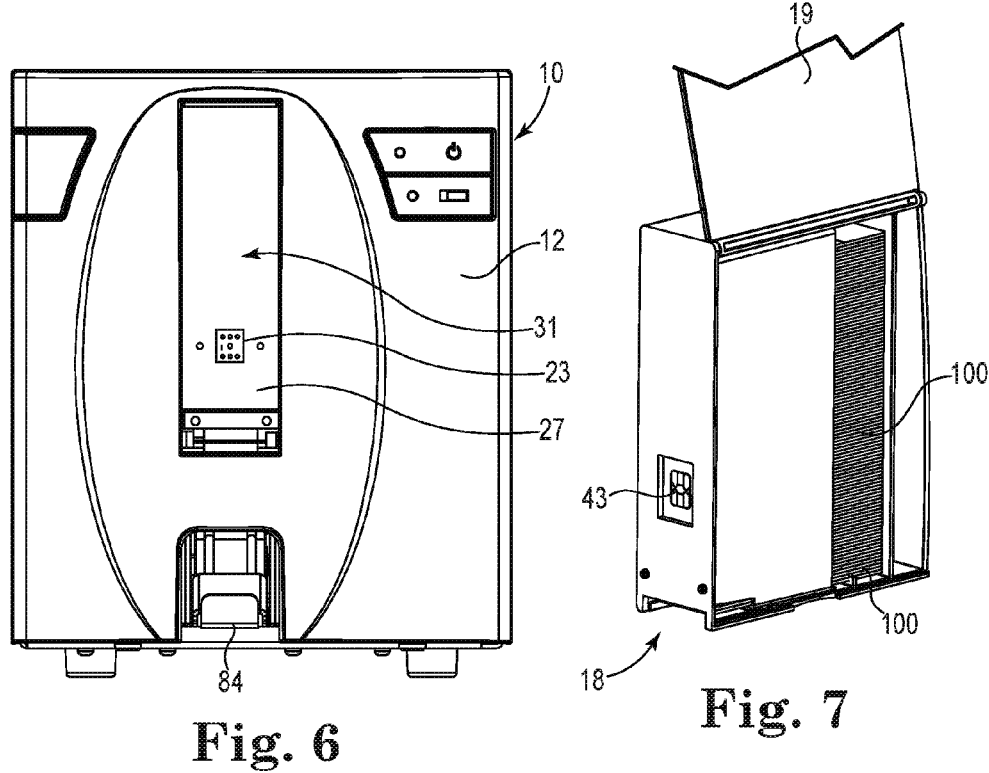
FIG. 6 is a front end view of the printing system shown in FIG. 1, with the slide cassette removed.
FIG. 7 is an isometric view of the slide cassette shown in FIG. 1

FIG. 6 is a front end view of one embodiment of the printing system 10, with slide cartridge 18 removed from the cabinet 12 to show the cartridge receiving area 31. As shown, an electrical contact 23 is mounted on a wall 27 at the back of the cartridge receiving area 31. The electrical contact 23 is coupled to the control system 34. FIG. 7 is an illustration of a slide cartridge 18 with its access cover 19 open and showing the slides 100 stacked therein. The illustrated embodiment of the cartridge 18 has a memory chip 43 mounted to its back wall. The memory chip 43 is mounted to the cartridge 18 at a position that will enable the memory chip to electrically contact or otherwise be coupled for data transfer with the electrical contact 23 on the printing system 10 when the cartridge is inserted into the enclosure 12.

Figure 8:
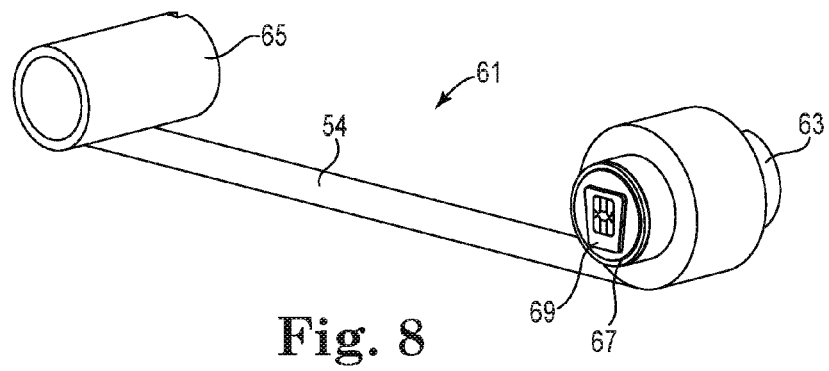
FIG. 8 is an isometric view of a print ribbon that can be used in the printing system shown in FIG. 1.
Figure 9:
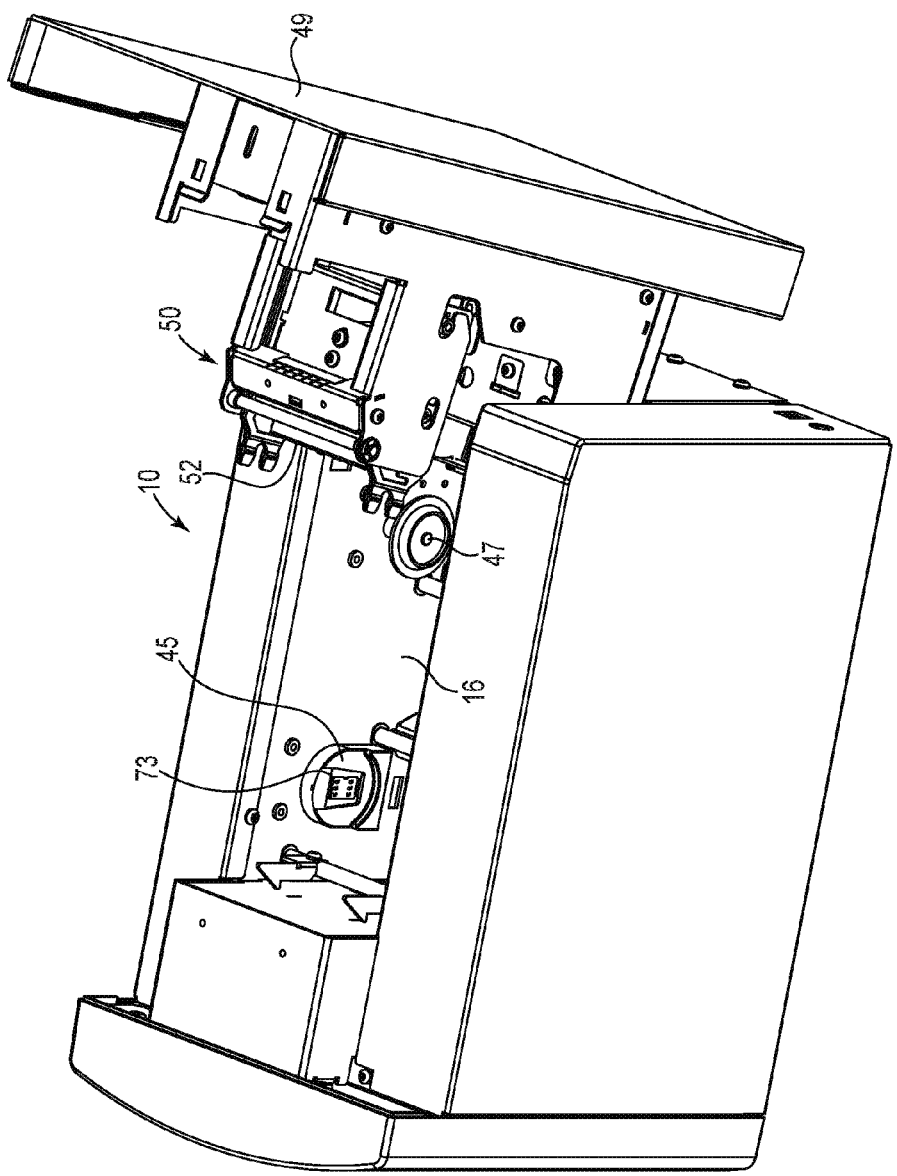
FIG. 9 is an isometric view of the printing system shown in FIG. 1 with the cover open.

FIG. 8 is an illustration of a print ribbon assembly 61 that can be used with the slide printing system 10. As shown, the print ribbon assembly 61 includes supply spool 63, take-up spool 65, and multi-color thermal ink ribbon 54. The composition of thermal ink ribbons such as 54 is generally known. As described above, in one embodiment of the invention the ribbon 54 has a plurality of primary color ink blocks (e.g., yellow, magenta and cyan) and black ink blocks (not separately shown in FIG. 8) spaced in repeating sequences along its length. Rotatably mounted to the supply spool 63 is a hub 67. A print ribbon memory chip 69 is mounted to the hub 67 in this embodiment. FIG. 9 illustrates an embodiment of the printing system 10 where the print ribbon supply hub 45 includes an electrical contact 73 configured for electrical coupling to the memory chip 69 on the supply spool 63. The print ribbon assembly 61 is loaded onto the print ribbon receiving structure by mounting the supply spool 63 to the supply hub 45, and mounting the take-up spool 65 to the take up hub 47. The memory chip 69 on the supply spool 63 is electrically coupled to the ribbon supply chip contact 73 when the supply spool 63 is mounted to the supply hub 45.

When the printing system 10 is switched ON the control system 34 can access information on the slide cassette memory chip 43 through electrical contact 33, and can access information on the ribbon supply memory chip 69 through the electrical contact 73. Information stored on the slide cassette memory chip 43 can include, for example, one or more of slide type and the number of slides remaining in the cartridge 18. Similarly, information stored on the ribbon supply memory chip 69 can include ribbon type, the number of images remaining on the ribbon 54, production date and/or batch no. Other or additional types of information can be stored on memory chips 43 and 69 in other embodiments. Information on the memory chips 43 and 69 is used to control the operation of printing system 10, and can be updated after print operations. For example, if the information on memory chips 43 or 69 indicates that the supply of slides or ribbon is exhausted, the control system 34 will not execute a requested print operation. Information stored on memory chips 43 or 69 representative of the number of remaining slides and the number of images remaining on the ribbon 54 can be updated following each print operation. If the types of slides and print ribbon loaded into the printer are not compatible, the unsuitable combination can be identified and an informational message can be provided and/or printing can be discontinued to reduce errors.

In summary, the printer will have an input area that holds unprinted slides with a frosted area (typically white) used to record data. The slides will be contained in a cartridge that will hold slides. An input feed roller will drive one slide out of the cartridge and move it towards the printhead. A slide position sensor will locate the slide as it exits the cartridge and allow the controls to control the drive rollers to precisely locate the printable area of the slide under the printhead. The ribbon drive motor will then advance the multiple color panel ribbon until the leading edge of the first color panel of the sequence (typically yellow in a YMCK ribbon) is positioned under the printhead as well. A ribbon sensor detects the transition between the color blocks on the ribbon and allows the control system to indicate to the printer the location of each color block on the ribbon relative to the printhead. When both the slide and the ribbon are in the proper location, the printhead will be lowered and the drive rollers and the platen roller will advance the slide as the first color panel is printed. The printhead will be raised by a cam, the slide will back up until the leading edge is under the printhead and the color ribbon will be advanced until the leading edge of the next panel is under the printhead. Then the printhead will lower and the drive rollers will advance the slide as the second color panel on ribbon is printed. This process will repeat for the remaining color panels. Once all of the color panels have completed printing, the drive rollers will advance the slide until it exits the printhead area and is transferred to a conveyor belt which will move the slide to the output hopper located on the front of the machine directly under the input cartridge.

The data for the slide can either be manually entered at a computer or a histology tissue cassette with a bar code containing all pertinent information that can be scanned to obtain the required data to be reprinted on slides.

Figure 4:
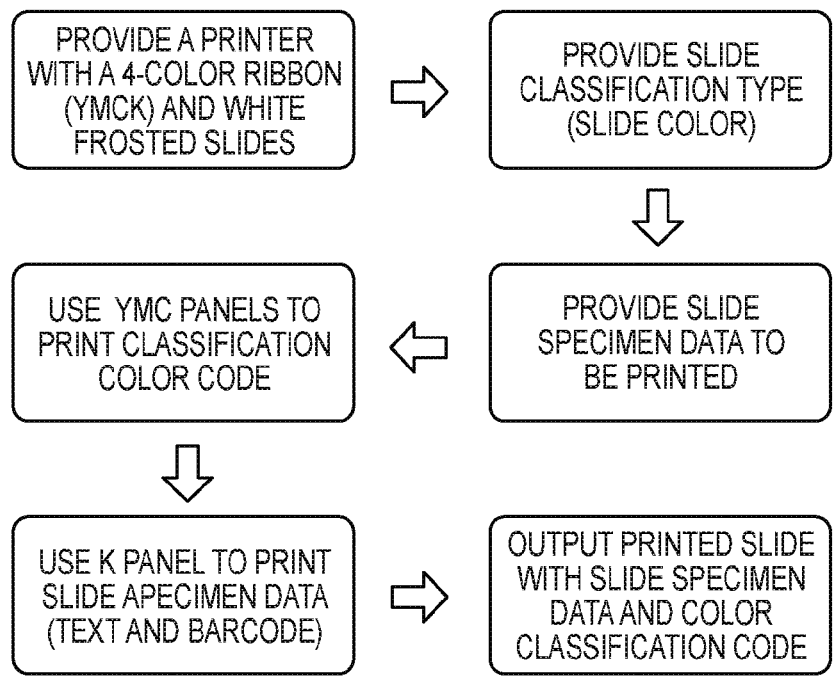
FIG. 4 is a block diagram of an operational sequence that can be used with the printing system shown in FIG. 1.

The sequence of operations in FIG. 4 shows the steps in the process using the colored ribbon for printing.

The invention provides for a printing system that includes a cartridge for holding a number of medical slides or histological slides on which tissue samples or other medical samples are to be placed, and which will be provided to a printer that will print in color on the slide for further identification of the class of tissue or sample that is to be placed onto the slide, as well as printing information about the specimen on the slide. This includes printing a bar code and/or text containing the data necessary for use of the slide, such as case number, patient name, year, issue class, priority rating etc. The slides will be prepared with an ink receptive surface, such as frosting the areas where there will be printing.

The slides are loadable in a cartridge so that they can be handled without getting fingerprints on the slides themselves, and multiple cartridges can be used, each to store slides for a different classification of specimens to be mounted on slides. The cartridges then can be easily identified as to the class of the specimen and the cartridge switched while keeping the slides dust and fingerprint-free.

The printer utilizes a series of drive rollers for carrying slides individually from the cartridge, and feeding them into a print station that includes a platen roller that supports the slide for printing and a printhead that prints the information on a surface opposite from the platen roller. The slide can be moved back and forth by suitable drive rollers for multi-color printing, or black and white printing, and when the information has been printed into the slide, the slide is removed from the print station (the printhead is lifted away from the slide as it is moved for printing and out of the print station) and then the slide is transferred to an output bin. The finished slide transfer device includes a conveyor belt that will receive the slides and transport the printed slides to a bin. Other types of storage can be provided as well.

The printhead is controlled by suitable software that will print an identifying color mark, in a bar or strip form onto the slide, and then the data that is required, including a text and the bar code for identification is printed on the slide, and this is generally done in black printing. A control system is used for coordinating various movements with the printing operations, including controlling the lifting and lowering of the printhead, the motors for the slide drive rollers, and the platen roller for multiple pass printing to print the desired identification information on the slide.

Although described in connection with embodiments of a thermal printer, those of skill in the art will recognize that the invention can be implemented in still other embodiments. For example, other embodiments of the invention can be implemented in inkjet, laser or other printers. One or more single color ink ribbons can be used instead of the multiple color panel ribbon. The printhead can be a separate printhead for each ink ribbon instead of the single printhead shown in the illustrated embodiment. Any and all of the fields of information on the slides can be printed in any desired color, and the printed color can be selected to represent information such as tissue type and source (e.g., the text and/or bar code can also be printed in color). Printing can also be done in one, two, three or more colors on each slide, with sequentially printed slides having the same or different printed colors. The printer can also be used with other slides, such as slides having a colored printing area.

Cassette 500

A histological tissue carrying cassette in accordance with one embodiment of the invention and indicated at 500 can be described with reference to FIGS. 10-14. As shown, cassette 500 includes a base 511 having a bottom wall 512 that has a number of openings 514 formed therein and which provide for drainage. The bottom wall 512 is surrounded by four upright side walls when a rectangular configuration is utilized, including a pair of side walls 516, a rear wall 518 and a front wall 520.

A tissue sample holding compartment 522 is thus formed by the side walls 516, rear wall 518 and front wall 520. The rear wall 518 has a guide opening 526, and there is generally a U-shaped wall 524 formed on the interior of the compartment to shield the opening 526 in the rear wall. Additionally, a partial offset wall portion 527 is provided in alignment with a slot 528 in one of the side walls 516, as shown. The slot 528 provides a structure of feeding the cassettes 500 from a stack into a processing station. In the embodiment of the cassette printer 200 described below, for example, the slot 528 is configured to be slidably engaged by a cassette loading rod that can hold a stack of the cassettes and be releasably inserted into the printer.

A lid 530 is molded as a unit with the base 511 and after molding is integrally attached to an upper edge of the rear wall 518 with a thin (reduced thickness of material) frangible hinge 532 formed during molding. The frangible hinge 532 extends across the upper edge of the rear wall 518, except in locations where there are recesses for guide projections or lugs that will be explained. The lid 530 has a rim 534 that will fit inside the upright walls 516, 520 and 518 of the base 511, and there is a flange 536 that surrounds the rim 534 and will rest on the top edges of the respective upright walls of the base. One side of the frangible hinge 532 is molded to the upper edge of wall 518 and the other side of the frangible hinge is molded to the mating or adjacent edge of the lid 530. The frangible hinge has a defined, selected length between the edge of wall 518 and the mating edge of the lid 530.

The lid 530 is provided with perforations or slots 538, which correspond generally in alignment with the slots 514 in the bottom wall 512 of the base 511.

Figure 10:
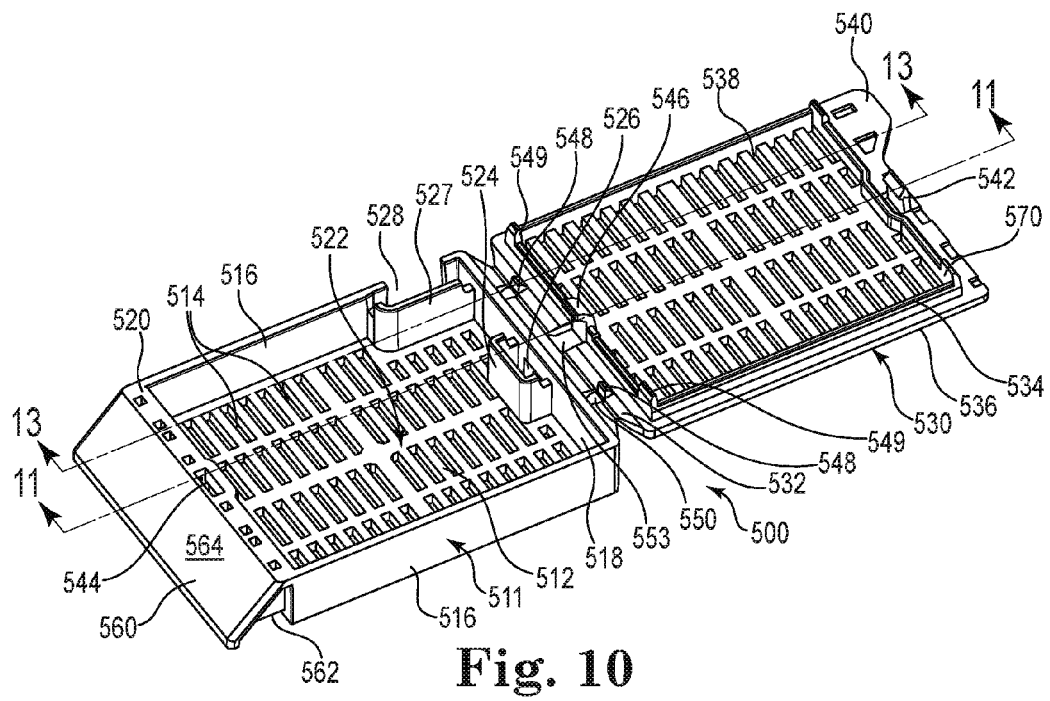
FIG. 10 is an isometric view of a molded tissue cassette in accordance with one embodiment of the invention, shown with a lid attached to a base in an open position.

In addition, a flange 540 on the end of the lid 530 opposite from the hinge 532 is of size to fit over the top of the front wall 520, and carries a latch dog 542 that will fit into a latch receptacle 544 in the top side of the front wall, as shown in FIG. 10.

Figure 13:
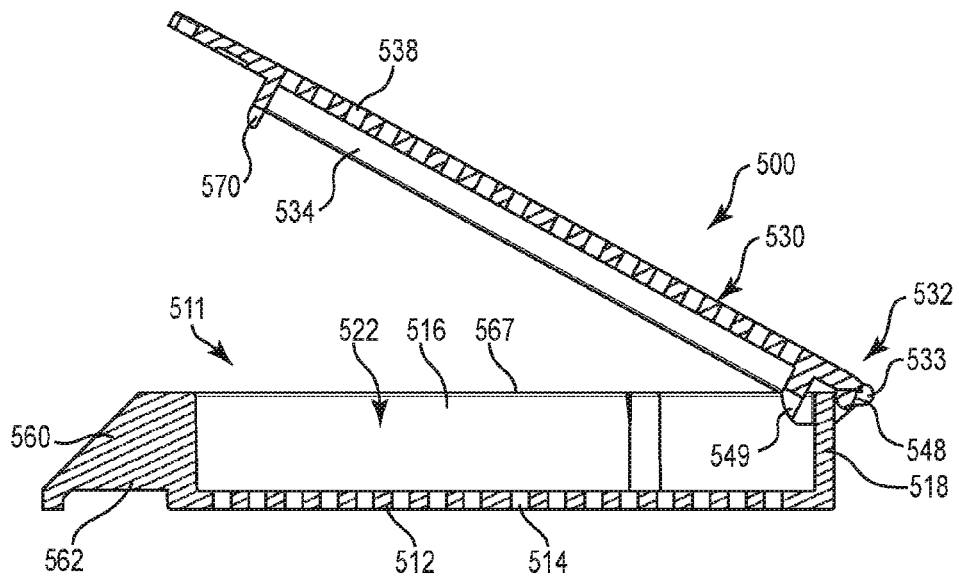
FIG. 13 is a sectional view of the cassette taken long line 13-13 in FIG. 10, showing the lid in a partially closed position.

The rear portion of the lid 530, adjacent the frangible hinge 532 has a projecting guide finger 546 that is curved and configured to fit into the opening 526 in the rear wall 518 as the lid is closed, as will be further shown. The lid 530 also has guide projections or lugs 548 at the rear edge, that will fit into openings 550 formed on a flange on the upper edge of the rear wall 518 to maintain the lid in position when it is initially closed, and also when it is subsequently closed after having been removed. The lugs 548 keep the lid 530 from sliding forward once the hinge 532 is fractured. There are guide projections or lugs 549 formed on the lid corners near the hinge 532 that will pass to the interior of the rear wall 518, as shown in FIG. 13. These guide projections or lugs 549 keep the lid 530 from sliding backward. The lugs 548 and 549, in conjunction, also insure that the lid 530 will stay square with the base 511 during closure, and as the latch dog 542 enters the opening 544 and latches under a suitable shoulder surface 544A on the front wall 520 below the opening 544.

The frangible hinge 532 is separated into four width segments, interrupted by the openings or apertures 550 and an aperture 553 by the center guide finger 546. The frangible hinge 532 includes a thin section 533 of molded plastic, and for example it could be in the range of 0.014 inches thick, and the hinge also includes a flange 556 extending outward from the rear wall 518 of the base and a flange portion 558 on the adjacent edge of the lid that is in line with and joins the flange 536 around the perimeter of the lid.

The front wall 520 has a front panel 560 integrally molded with the upper edge of the front wall and inclined relative to the upright wall. The panel 560 is supported with suitable gussets 562 extending back to the front wall 520. The upwardly facing surface 564 of the panel 560 is molded smooth, so that it can be used for printing on the surface to identify the specimen or tissue sample that is contained in the compartment 522 of the base 511.

It can be seen that the flange 556 (See e.g., FIGS. 11-13) extends rearwardly from the rear wall 518, and has a surface portion 566 that slopes downwardly from the plane defined by the upper edges of the side and end walls of the base 511. The upper wall edges define a plane and are indicated at 567 in FIGS. 11 and 12.

Figure 11:
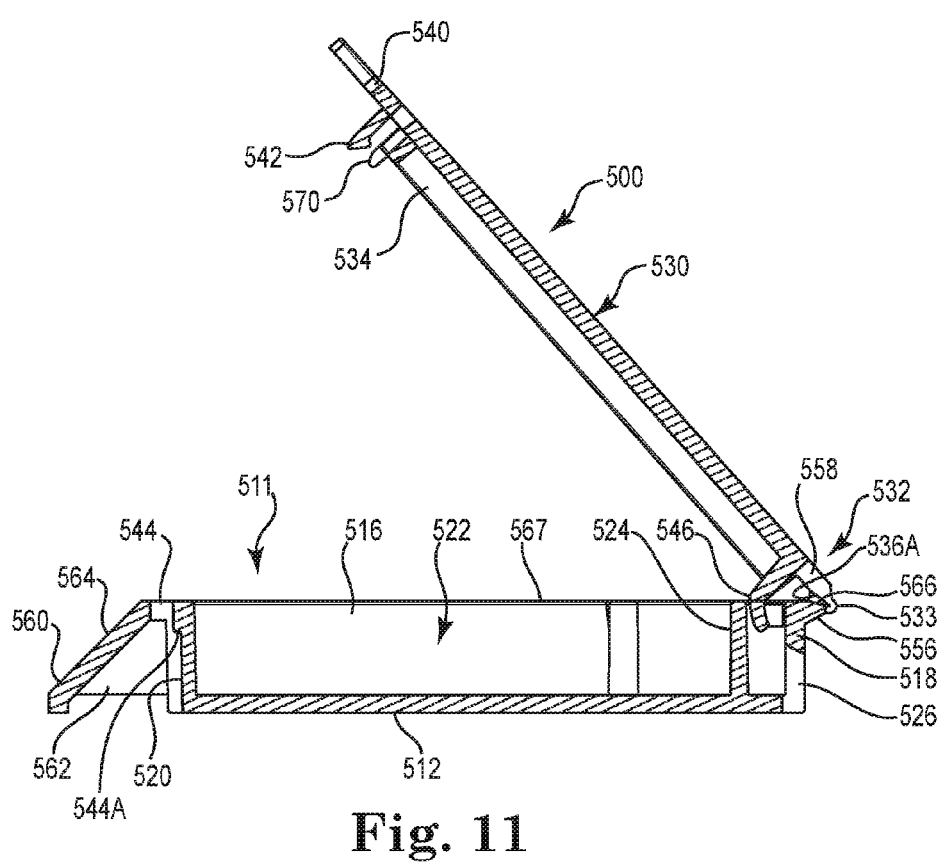
FIG. 11 is a sectional view of the cassette taken along line 11-11 in FIG. 10, showing the lid in a partially closed position during the initial closing and before fracturing a hinge member.
Figure 12:
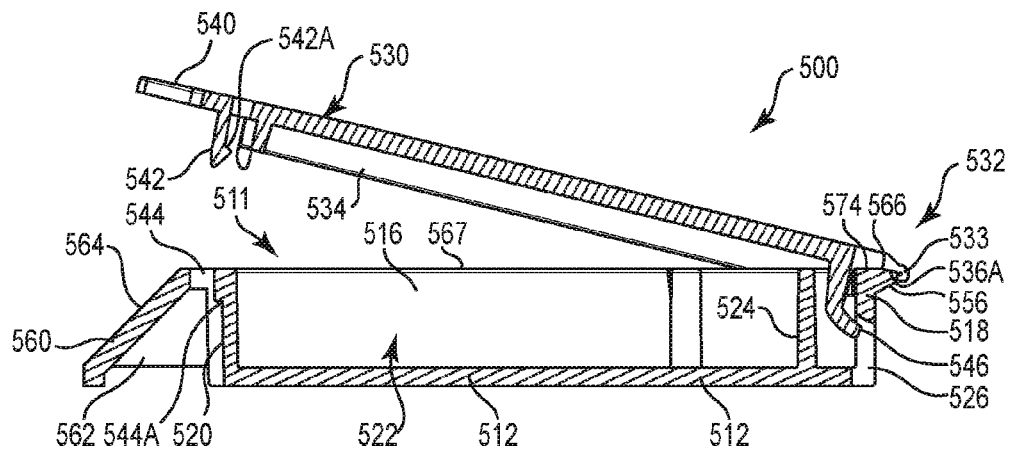
FIG. 12 is a sectional view of the cassette taken along line 11-11 in FIG. 10, showing the lid moved further toward a closed position relative to a cassette base.

As shown in FIGS. 11, 12 and 13, as the lid 530 is hinged from the position shown in FIG. 10 to a closed position during its first closing, the hinge 532 will fold as shown in FIG. 11, and the guide finger or projection 546 will pass into the space defined by the U-shaped wall 524, as shown in FIGS. 11 and 12. When the lid 530 reaches its position as shown in FIG. 12 as it is closed, it can be seen that a portion 536A of surface 536 on the underside of the flange at the rear or hinge end of the lid will come to rest on the surface 566, and that the surface 536A is inclined so that when it comes to rest on surface 566 the lid 530 is not fully closed, and the hinge 532 is still intact.

During the closing process, as also shown in FIG. 13, which is a sectional view at a different location from FIGS. 11 and 12, the lugs 548 on the lid 530 will slide to a position where they are to the exterior of the rear wall 518, and will prevent the lid 530 from sliding forwardly as it is closed. The lugs 549 will prevent the lid 530 from sliding rearwardly. Also, for side to side guiding, there are lugs 570 at opposite corners of the lid adjacent the latching end, or front end, and these will fit within the space between the side walls 516 to keep the cover oriented relative to the base during closure and as the front latch dog 542 moves to a latched position.

Figure 14:
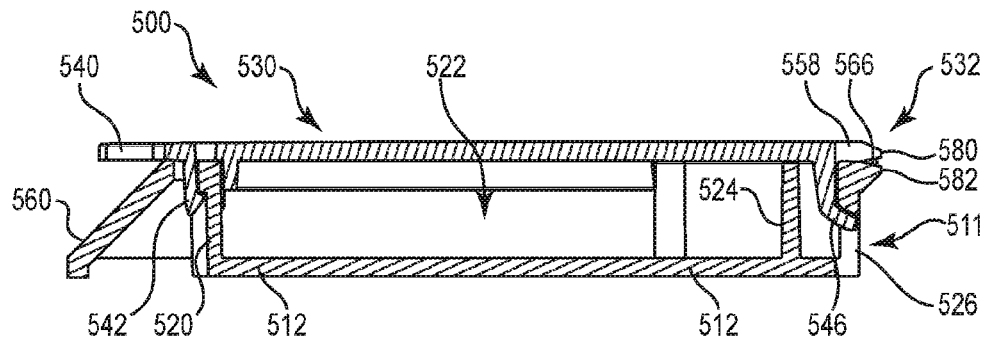
FIG. 14 is a sectional view of the cassette taken along line 11-11 in FIG. 10, showing the lid in a fully closed position and illustrating the fracturing of the hinge caused by the initial closing.
Figure 15:
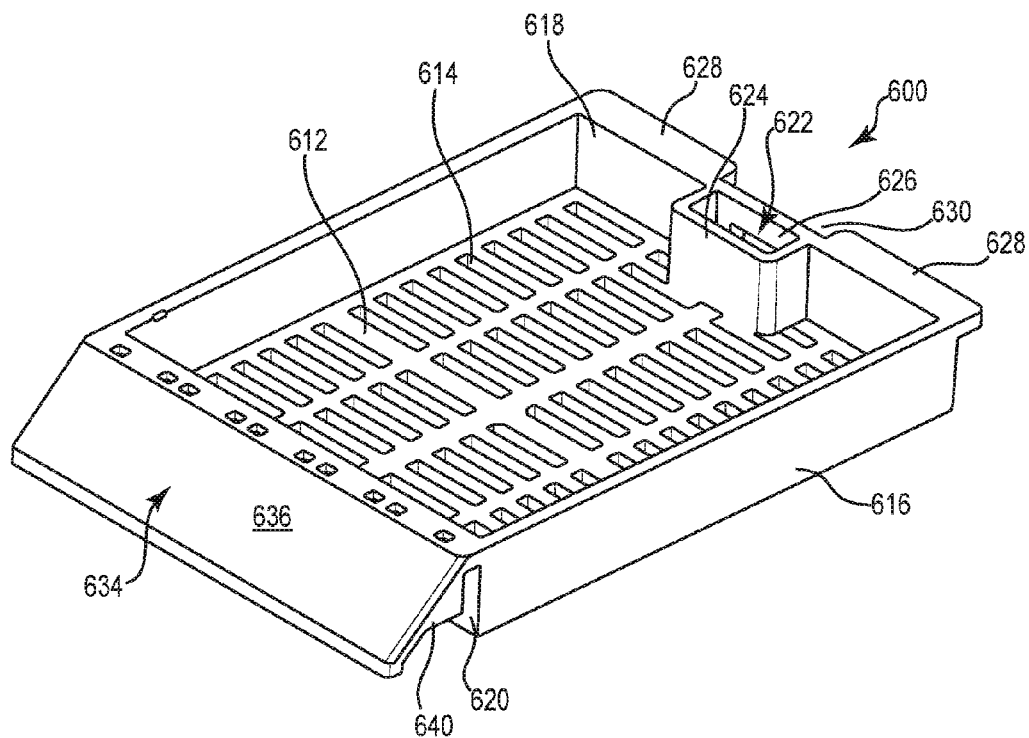
FIG. 15 is a front isometric view of a molded tissue cassette in accordance with another embodiment of the invention showing a print-receptive, information display panel.
Figure 16:
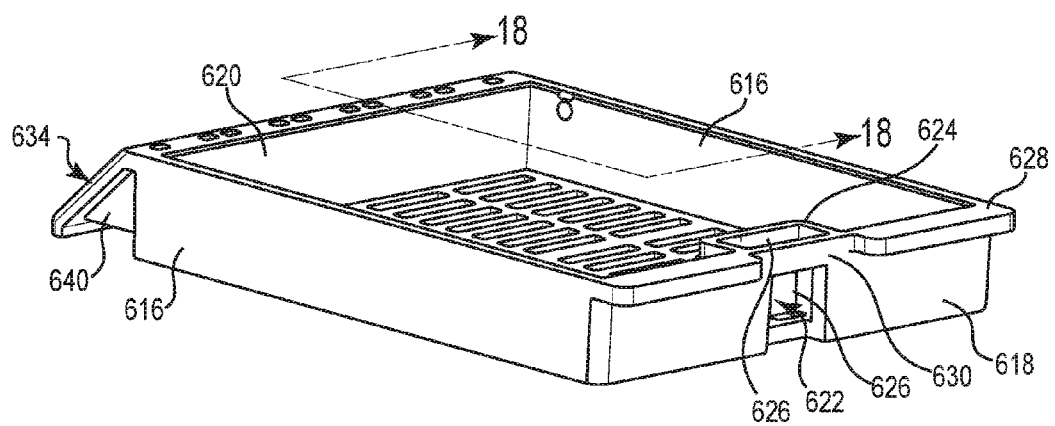
FIG. 16 is an isometric view from a rear side of the cassette shown in FIG. 15.

As the lid 530 is moved between the positions shown in FIGS. 13 and 14, the flange portion 558 will rock or pivot on the upper surface 566 of the protrusions 556 on the base, and the surfaces are configured to create a tension force in the thin section 533 of the hinge 532 as the flanges 556 and 558 move apart as the lid is closed. When the lid 530 is completely closed as shown in FIG. 14, the frangible hinge 532 has ruptured under tension loads because of the configuration of the mating surfaces 566 and 536A that spaces the ends of the flanges 556 and 558 joined to frangible hinge 532 a greater distance than the length of the molded, thin hinge material 533 between the wall and lid edges. The lid is thus positively physically separated from the base 511 and is no longer connected to the base by a hinge. The lid 530 is, however, held by the guide finger 546 sliding along a curved surface defining the opening 526 in the rear wall 518, as also shown in FIG. 14.

It should be noted that the tension force put on the frangible hinge 532 can be large and controlled because of the leverage that is generated by the contact of the junction line 574 at the edge of surface 536A that forms a fulcrum to cause the outer edge of the lid to move vertically relative to the base as the lid closing motion continues from the position in FIG. 12 to the position of the lid in FIG. 14. The outer end of the flange 558 portion is lifted relative to the flange 556 and the tension force in the hinge as it is stretched is sufficient to rupture the hinge section 533. The distance between the outer tip of the flange portion 558, which is shown at 580 in FIG. 14, and the outer tip of the protrusion 556, shown at 582, is greater than the length of the hinge section 533 so that the positive tension force will cause a rupture reliably and without any likelihood of having the hinge not separate completely when the lid is initially closed to its position shown in FIG. 14.

The latch dog 542 has a surface 542A that will fit under a shoulder 544A on the front wall 520, just below the opening 544, after the latch dog has been passed through the opening 544 in the ledge at the upper edge of the front wall 520.

The unitary molded cassette can be used for mounting tissue samples, and has a lid that can be integrally molded with the base, through a hinge that will reliably rupture when the lid is moved to its first closed position. Removing the lid from the base as a separate unit after the initial closure merely requires unlatching the latch dog from under the ledge of the front wall, and then lifting the lid as guided by the guide finger 546 and the surfaces of the opening 526.

The lid can easily be replaced again by placing the lid rear portion so that the guide finger 546 passes into the recess formed by the wall 524, and then through the opening 526, as it is pivoted closed. The lugs 548, 549 and 570 serve to position the lid 530 as it is closed.

In summary, one embodiment of the invention is a molded tissue cassette comprising a base having a compartment for holding tissue samples and a lid for covering the compartment that is initially unitarily molded to an upper edge of one wall of the base with a molded frangible hinge. The lid is constructed so that the frangible hinge will be fractured under tension loading as the lid is first hinged to its position to cover and overlie the compartment. The lid has a surface that rests on the upper surface of the one wall of the base and forms a pivot as the lid is first closed to create a tension load in the frangible hinge to fracture or rupture the hinge in tension, and also has suitable molded guides cooperating with portions of the base to precisely guide the lid into the closed position. The guides and a latch dog will precisely hold the lid in position after it has been removed from the base as a separate part and is replaced after the hinge is fractured.

Cassette 600

A histological tissue carrying cassette 600 in accordance with another embodiment of the invention can be described with reference to FIGS. 15-19. As shown, cassette 600 includes a bottom wall 612 that has a number of openings 614 formed therein, which provide for drainage. The bottom wall 612 is surrounded by four upright side walls, when the rectangular configuration is utilized, including a pair of side walls 616, a rear end wall 618, and a front end wall 620. The four upright walls are secured to, and molded integrally with the bottom wall 612 from a suitable plastic.

A compartment 622 is formed in relation to a rear wall with a general U-shaped wall 624. In the space defined by the size of the U-shaped wall 624, there are openings 626. The rear wall also has horizontal ledges 628 at the top edge defining a slot 630 between the ledges.

The front wall 620 has a molded front panel 634 attached and integrally molded with an upper edge of the front wall 620. The panel 634 is inclined at substantially a 45° angle relative to the upright wall 620, and has an upper surface 636 on which printing to identify the tissue sample that would be held in the cassette is placed. The printing can include a bar code, and text that identifies the tissue sample as to its type and source, and can include information relating to tests to be performed, for example.

Figure 17:
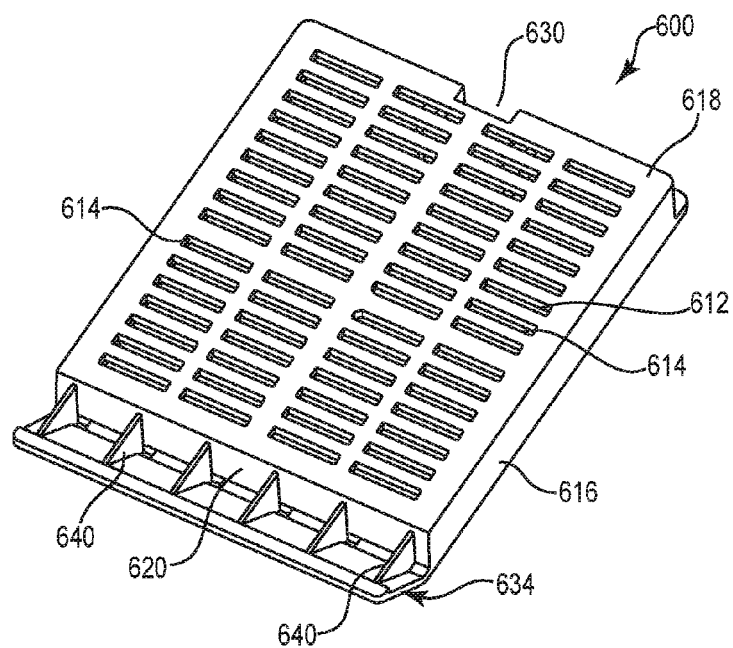
FIG. 17 is an isometric view from the bottom of the cassette shown in FIG. 15, showing support ribs or gussets for supporting the display panel on which information is to be printed.
Figures 18, 19:
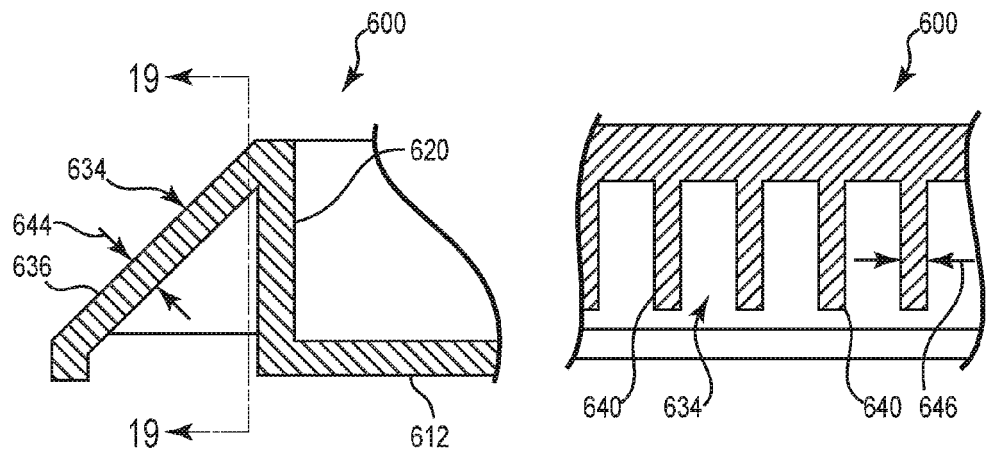
FIG. 18 is a detailed sectional view of the cassette taken along line 18-18 in FIG. 16.
FIG. 19 is a detailed sectional view of the cassette taken along line 19-19 in FIG. 18

Panel 634 is a print-receptive panel on which information is placed, and in order to print satisfactorily, particularly with thermal printing heads, the surface 636 must be flat, as well as smooth. In order to accomplish a flat, smooth surface 636 from a molded plastic cassette made out of suitable plastic, without further finishing, the present invention optimizes the size and placement of the ribs relative to the thickness of the panel 634 to support the panel. As shown, panel 634 is supported with a plurality of ribs 640 that, as shown in FIG. 17, are secured to the front surface of the front wall 620, and then also supports a rear surface of the print-receptive panel 634.

In prior cassettes, it has been found that as the plastic cools after molding, the panel will tend to bend and warp for a variety of reasons. In many cassettes the side walls are continued forwardly at the same thickness to support the printable panel at the ends of the panel, and thus at least these end supports are relatively thick.

When combined with thinner support ribs between the side walls, the print-receptive panel is supported by walls of varying thickness. Because walls of different thickness shrink different amounts when cooling after molding, the print-receptive panel will be necessarily pulled out of flat. Also, where a wall of substantially the same thickness as the print-receptive panel joins the panel at its end, thus forming an "L", cooling after molding tends to pull the walls toward each other, thus also tending to pull the panel out of flat.

Some prior cassettes also have ribs that are too thick relative to the thickness of the print-receptive panel. In these cassettes, the extra plastic present behind the print-receptive panel at the locations of the ribs causes the plastic to sink, or indent, in these areas during cooling after molding.

Typically, prior cassettes also do not have enough ribs to adequately support the print-receptive panel for thermal printing. Many only have two ribs and others do not have any. When the print head moves across these inadequately supported print-receptive panels, the pressure needed for good-quality printing cannot be generated, even if the print receptive panel is flat prior to printing.

No known prior cassettes have a sufficient number of closely spaced ribs of substantially equal thickness for satisfactorily supporting the print-receptive panel for thermal printing.

The present invention involves a structure in which the ribs 640 are a selected thickness relative to the thickness of the print-receptive panel 634, and a plurality of more than two are spaced across the entire width of the cassette, which is the length of the panel, and at locations that provide adequate support. This will yield a flat, smooth, and printable surface 636 on the panel 634.

The cassettes 600 generally, for standard uses, run approximately 1.1 inches in width, that is along the length of the panel 634. The ribs 640 have a thickness that is in the range of 32% to 59% of the thickness of the front panel 620. Generally, ribs that are 60% or less in thickness do not generate indents on the adjoining wall. In this case, the front panel, as shown by the double arrows 644 in FIG. 18, has a thickness of 0.04 inches, and the thickness of the ribs or gussets, as shown by double arrows 646 in FIG. 19 range between 0.013 and 0.024 inches. The difference in thickness of the ribs is due to draft, which is necessary to allow the cassette to be ejected easily from the mold.

For adequate support of the front panel, a spacing of 0.2 inches between center lines of the ribs 640 has been found to be satisfactory with the thicknesses provided and with a cassette width of 1.1 inches.

Using ribs that are substantially equal in thickness, carefully selecting the ratio of the thickness of the ribs to the thickness of the print-receptive panel, and providing a plurality of closely spaced ribs sufficient in number to rigidly support the print receptive panel provides a surface 636 on the print-receptive panel 634 that will be flat and smooth enough for printing without further machining or finishing after molding and cooling.

A lid or cover (not shown) is placed over the top of the cassette after the tissue sample has been put in place.

The plastic molded cassette, as disclosed therefore provides for a low cost cassette that can be used for containing tissue samples and which can be printed upon using thermal printing technology for identification purposes without further manufacturing procedures.

In summary, one embodiment of the invention is a molded tissue cassette comprising a cavity formed by four upright walls around a perforated bottom wall. One of the four walls has an integral molded print-receptive panel that is connected to the top edge of the one wall and is inclined outwardly and downwardly and is spaced from the upright adjacent wall.

The panel provides an upwardly facing surface for printing information about the tissue sample contained in the cassette. The information is readily readable by automated equipment, as well as being visible to a person looking at stacks of the cassettes in storage, for example.

The print-receptive panel is supported relative to the adjacent upright wall with a plurality of molded ribs or gussets that are spaced along the length of the panel. The ribs or gussets are all substantially the same thickness, and the thickness of the ribs or gussets selected is such that upon cooling they do not cause uneven shrinkage that leaves indents on the outer surface of the panel directly opposite the ribs or gussets. The number and spacing of the ribs or gussets is selected to insure that the panel does not warp along its length when cooling or in subsequent use.

Using only substantially equal thickness ribs or gussets to support the print-receptive panel, properly selecting the thickness of the ribs or gussets in relation to the thickness of the print-receptive panel being supported, and providing a plurality of the ribs or gussets sufficient to support the panel for thermal printing, insures that after cooling of the molded plastic, a flat and smooth panel surface for printing is provided without subsequent processing, such as grinding, polishing or sanding. Since ribs or gussets of differing thickness will shrink different amounts in the molding process, they must be substantially the same thickness to achieve a flat print-receptive panel. Also, ribs or gussets that are too thick relative to the print-receptive panel that they support will cause indents in the panel directly opposite the ribs or gussets due to uneven cooling and therefore uneven shrinkage.

Although cassette 600 is described as a separate embodiment from cassette 500, features of these two cassette embodiments are combined in other embodiments of the invention. For example, the print panel and support gussets of the cassette 600 are incorporated into the cassette 500 in other embodiments of the invention. Similarly, the lid and frangible hinge of the cassette 500 can be incorporated into the cassette 600. Other variations will also be apparent to those skilled in the art. For example, although described as unitary molded members, other embodiments of the cassettes can be assembled from separately manufactured components.

Color Cassette Printer 200

Figure 20:
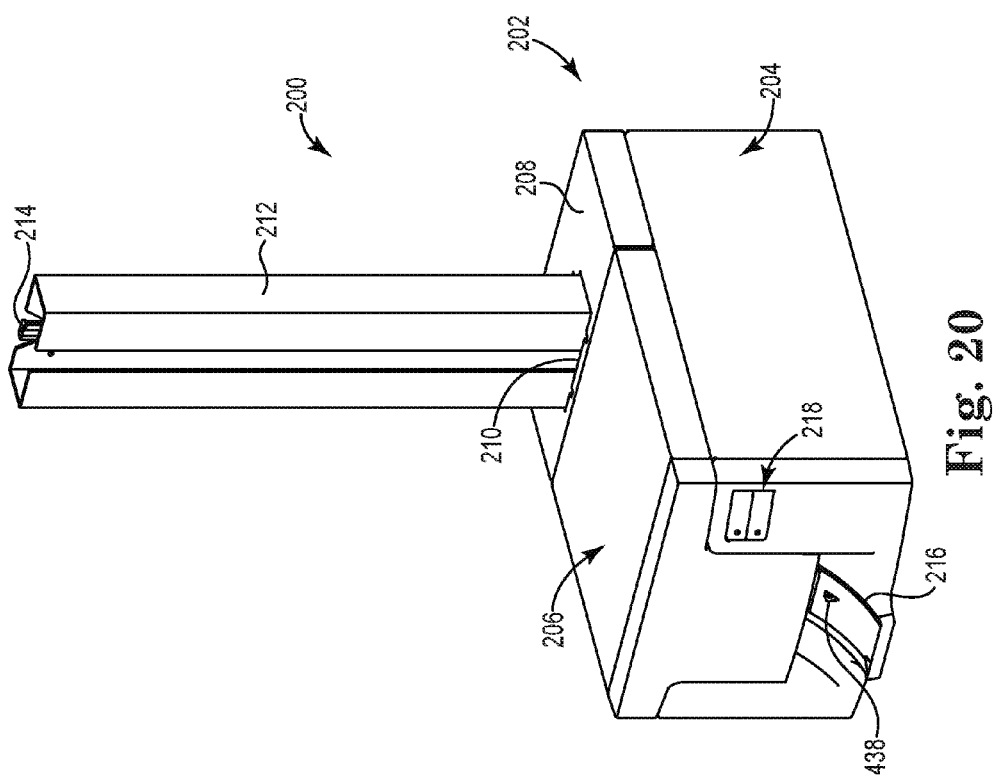
FIG. 20 is an isometric view of a cassette printer in accordance with one embodiment of the invention.

A color cassette printer 200 in accordance with another embodiment of the invention can be described in connection with FIGS. 20-53. As shown in FIG. 20, cassette printer 200 has an enclosure 202 that includes a base 204, an access lid 206 on the top of a front end of the enclosure and a cover 208 on the top of a back end of the enclosure. An opening 210 in the cover 208 receives a hopper 212 and cassette loading rod 214. Specimen cassettes such as cassettes 500 and 600 and variations described above (not shown in FIG. 20) are fed into the printer 200 through the hopper 212 and loading rod 214. Cassettes with color printed specimen information are outputted from the printer 200 at a slide 216. As shown, an operator control panel 218 is also located on the front end of the printer 200. Cassette printer 200 can be used to print information on any of a wide variety of cassettes including, but not limited to those described herein.

Figure 21:
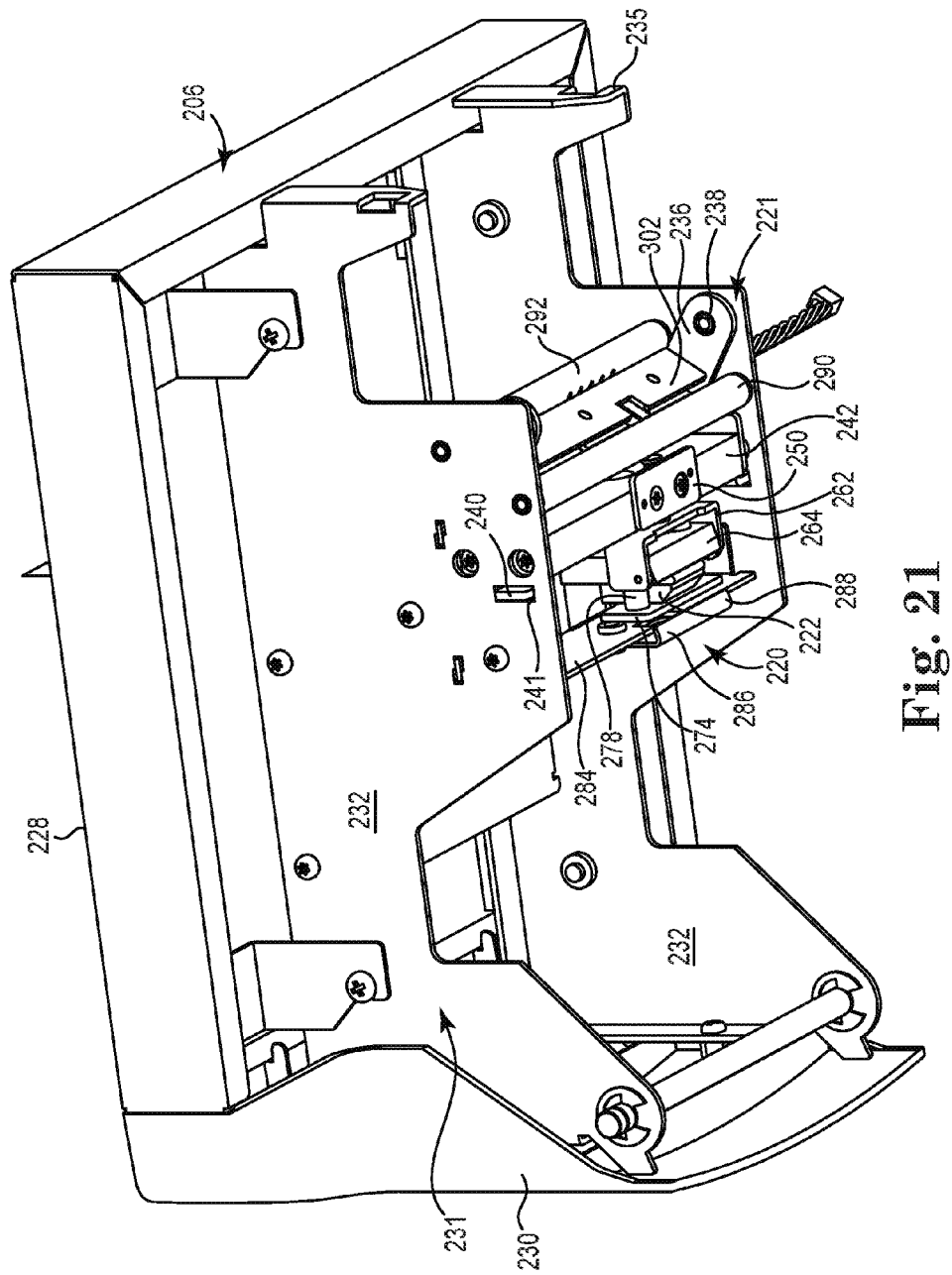
FIG. 21 is an isometric view of the inside of the lid of the printer shown in FIG. 20, showing the printhead assembly.
Figure 22:
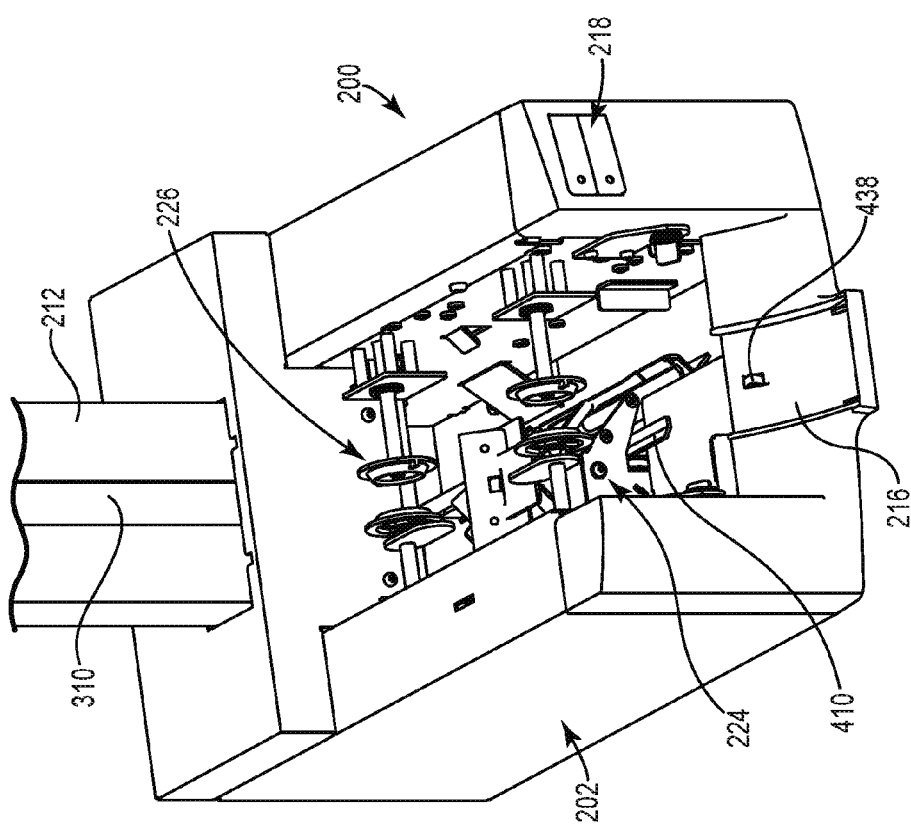
FIG. 22 is an isometric view of the printer shown in FIG. 20, with the lid removed and showing the cassette index assembly and print ribbon receiving structure.

The operation of cassette printer 200 can be briefly described in connection with FIGS. 20-24. Lid 206 is pivotally mounted to the enclosure 202, and as shown in FIG. 21 includes a printhead assembly 220 having a thermal printhead 222 mounted to its interior side. Lid 206 can be raised to provide access to a cassette index assembly 224 and a color print ribbon receiving structure 226 within the enclosure 202 as shown in FIG. 22 (the lid is not shown in FIG. 22). When the lid 206 is in the closed position, the printhead 222 is positioned at a printing position with respect to the cassette index assembly 224. During a printing operation the cassette index assembly 224 picks a cassette from the loading rod 214 and drives the cassette in a reciprocal manner along a printing path with respect to the printhead 222. The printhead 222 transfers multiple colors of ink from an ink ribbon 418 and prints specimen information in color on the cassette print zones. When the printing operation is completed the index assembly 224 outputs the printed cassette from the printer 200 by pushing the cassette to the output slide 216.

Figure 23:
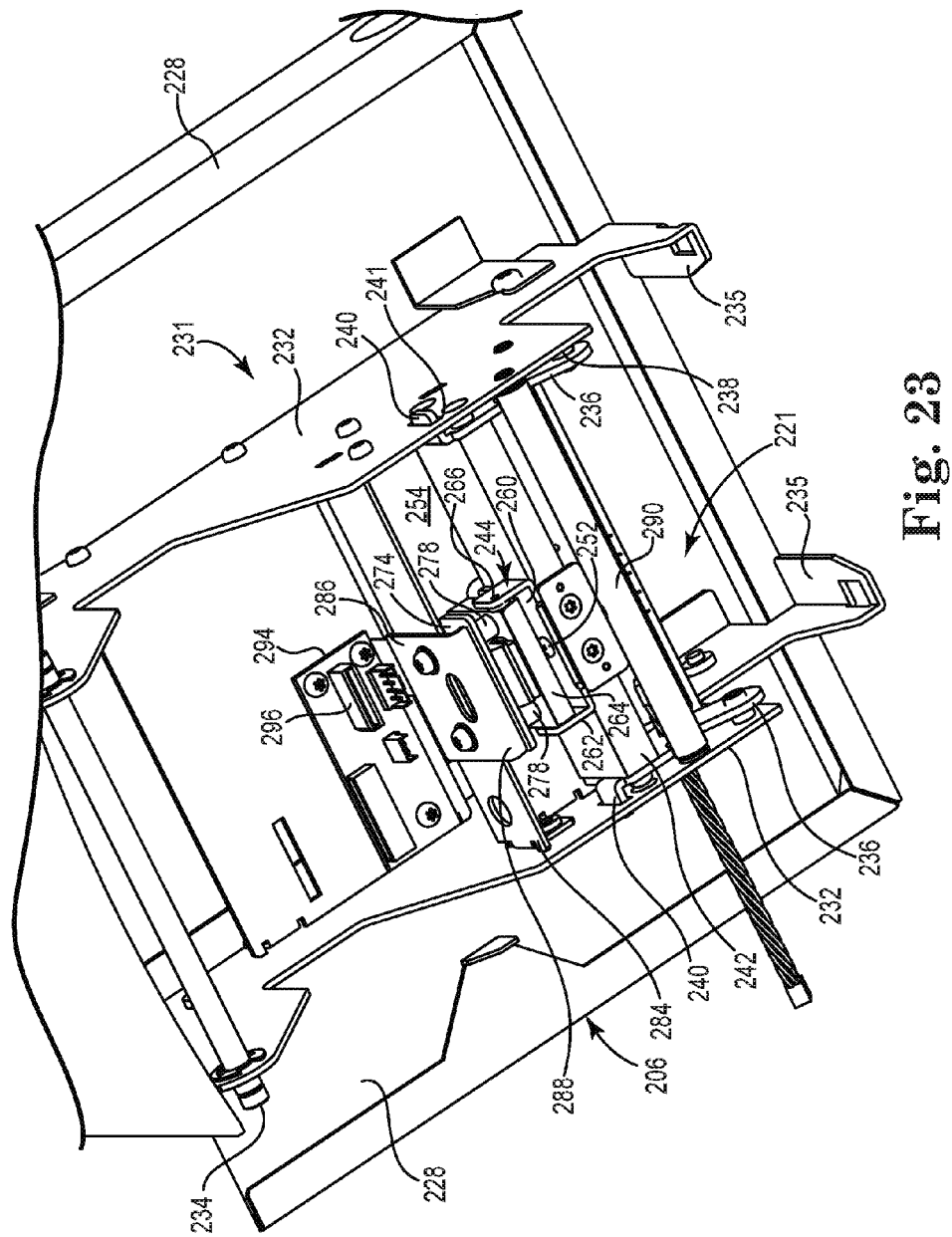
FIG. 23 is another isometric view of the inside of the lid of the printer shown in FIG. 20, showing the printhead assembly.
Figure 24:
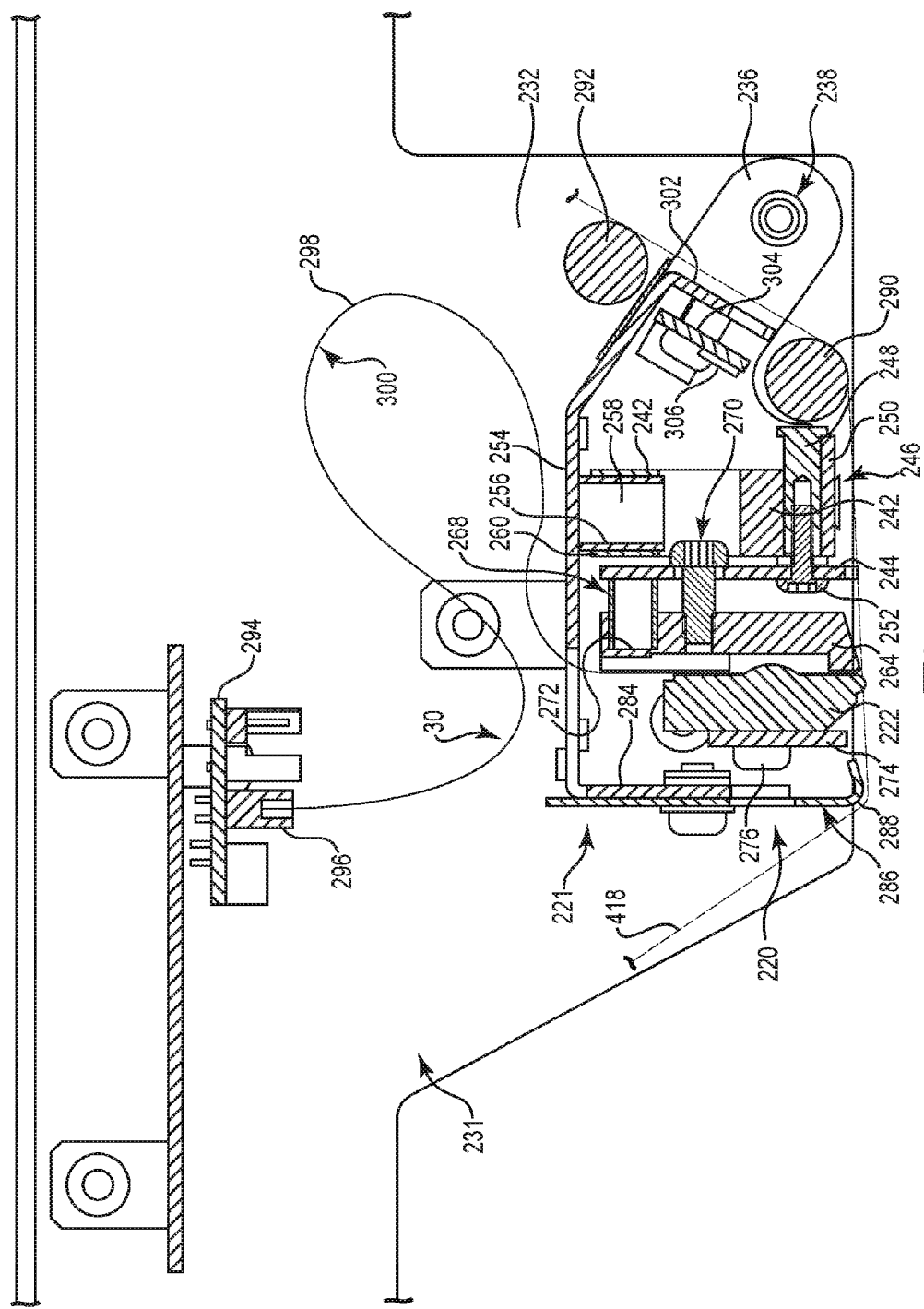
FIG. 24 is a cross sectional view of the lid and printhead assembly.

Lid 206 and printhead assembly 220 can be described in greater detail with reference to FIGS. 21 and 23-24. As shown, the lid 206 includes a top panel 228 and a front panel 230 supported by a main frame 231 formed by brackets 232. A shaft 234 extending between the brackets 232 pivotally mounts the lid 206 to the enclosure 202. Latch members 235 on the ends of the brackets 232 releasably engage the enclosure 202 to hold the lid closed 206 with the printhead assembly 220 positioned at the print position with respect to the cassette index assembly 224. The printhead assembly 220 includes a subframe 221 formed by a pair of brackets 236, each of which is pivotally mounted to one of the main frame brackets 232 by a pivot mount 238. The subframe brackets 236 have tabs 240 that extend through slots 241 in the main frame brackets 232 to limit the range of motion of the printhead assembly 220 with respect to the lid 206, and thereby also limit the range of motion of the printhead 222 with respect to the cassette index assembly 224. The position of the printhead 222 is generally fixed with respect to the cassette index assembly 224 in the printer 200 during printing operations. However, in the illustrated embodiment of the printer 200 the configuration of the subframe brackets 236 on the main frame brackets 232 enables the printhead to move over a relatively short distance (e.g., about 0.040 inches in one embodiment) to accommodate manufacturing tolerances and to enable a controlled printhead force to be applied between the printhead and cassettes during the printing operations as described below.

Crossbar 242 extends between and is mounted to the subframe brackets 236. Printhead pivot plate 244, which includes a base 260 and spaced apart tabs 262, is mounted to the crossbar 242 by a y-axis pivot mechanism 246 that allows the pivot plate and components described below including the printhead 222 mounted to the pivot plate to rotate with respect to the cassette index assembly 224 about a y-axis that is parallel to the printing path. The y-axis pivot mechanism enables the printhead 222 to accommodate variations in the planar position of the print zone of the cassettes and remain flat and parallel to the print zones during printing operations. In the embodiment shown the y-axis pivot mechanism 246 includes a y-axis pivot pin 248 that extends through the crossbar 242, a pin capture plate 250 and a screw 252. Other y-axis pivot mechanisms can be used in other embodiments of the invention (not shown). Mounted to the main frame brackets 232 and positioned above the printhead assembly 220 is a hood 254. A print force bias member, which is a spring 256 in the illustrated embodiment, is positioned in a compressed state in a recess 258 of the crossbar 242, between the crossbar and the hood 254. The print force bias spring 258 thereby applies a printhead force that urges the printhead assembly 220 and printhead 222 in a generally downward or z-direction toward the cassette index assembly 224 with respect to the hood 254 and lid 206. One embodiment of the invention uses a printhead force of about 1.3 lbs, but this force can vary depending on a range of factors such as the size of the printhead (which is e.g., 14 mm in one embodiment of the invention). Other embodiments of the invention (not shown) include other approaches for generating the printhead force during printing operations.

Printhead mount bar 264 is mounted between the tabs 262 of printhead pivot plate 244 for rotational movement about an x-axis by pivot pins 266. An x-axis adjustment mechanism including an x-axis bias member, which is a spring 268 in the illustrated embodiment, and an adjustment screw 270, adjustably fixes the position of the printhead mount bar 264 about its rotational axis. As shown, the x-axis bias spring is positioned in a compressed state in a recess 272 of the printhead mount bar 264, between the printhead mount bar and the base 260 of the printhead pivot plate 244. The printhead 222 is mounted directly to a printhead mount plate 274 (e.g., by screw 276). The printhead mount plate 274 is mounted to and supported from the printhead mount bar 264 by a pair of standoff mounts 278 that extend between the printhead mount bar and the printhead mount plate on opposite sides of the printhead 222. By rotating the adjustment screw 270, the printhead 222 can be rotated and positioned about an x-axis to adjustably fix the printhead heater line (not visible) at an optimized printing position. Other embodiments of the invention (not shown) have other x-axis adjustment mechanisms, or no x-axis adjustment mechanism if adjustment of the printhead heater position is not needed. Still other embodiments of the invention (not shown) include other structures for mounting the printhead 222. For example, the printhead 222 can be mounted more directly to the pivot plate 244.

A cross member 284 extends between and is mounted to the main frame brackets 232 at a location opposite the printhead 222 from the printhead mount bar 264. Ribbon deflector 286 is mounted to the cross member 284 adjacent to the printhead 222, and has a curved lower edge 288 to position the print ribbon 418 as it passes the printhead. A pair of ribbon guide rollers 290 and 292 also extend between and are rotatably mounted to the main frame brackets 232. Ribbon rollers 290 and 292 guide the print ribbon 418 on the side of the printhead 222 opposite the ribbon deflector 286.

A circuit board 294 having a connector 296 is mounted to the lid 206 with the connector located directly above (in the z-direction) the printhead 222. The electrical cable 298 extending from the printhead 222 is connected to the connector 296. The electrical cable is configured to have one or more loops 300 (one is shown in the illustrated embodiment) between the connector 296 and printhead 222. Because the cable 298 extends substantially only in the z-direction above the printhead 222 and has loop 300, the force exerted by the cable on the printhead assembly 220 is relatively low and generally centered on the rotational y-axis of the printhead so as to minimize interference with the printhead assembly.

A cross member 302 extends between and is mounted to the subframe brackets 236 at a location between the ribbon rollers 290 and 292. A circuit board 304 is mounted to the cross member 302 and has an optical sensor 306 mounted thereto. Optical sensor 306 is located to detect light emitted by LEDs 429 (shown, e.g., in FIG. 43) and transmitted through the print ribbon 418. As described in greater detail below, the detected light signals produced by sensor 306 are used by the printer control system 434 to track the color panels on the print ribbon 418 and to detect the end of the print ribbon.

Hopper 212 and the manner by which it is releasably mounted to the printer 200 can be described with reference to FIGS. 25-28. As shown, the hopper 212 is a tubular member formed from a pair of spaced-apart U-shaped members 308 secured together on one side by brackets 309 to provide elongated slots 310 and 311 on the front and back sides, respectively. The hopper 212 has a cross sectional shape that receives the cassettes in the configuration of the cassettes when loaded on the loading rod 214 (e.g., with the cassette lid open and the lid and cassette base generally flat or planar as shown in FIG. 28). As described in greater detail below, the slot 311 on the back side of the hopper 212 functions as a structure for releasably receiving and engaging the cassette loading rod 214. The bottom of the hopper 212 has an opening 312 on the front side. The hopper 212 extends through the opening 210 in the cover 208 and is releasably engaged to structures within the enclosure 204 with the bottom end and opening 312 located adjacent to the cassette index assembly 224.

In the illustrated embodiment, a releasable latch structure includes one or more first members such as pins 314 on the bottom of the hopper 212 (four are shown in the illustrated embodiment) and one or more second members such as pin-receiving latches 316A and 316B that are mounted to bracket 318 in the enclosure base 204. Pins 314 cooperate with latches 316 to securely retain the hopper 212 in position in the printer 200, yet to allow the hopper to be inserted into and removed from the printer by hand without the use of tools.

Figure 27:
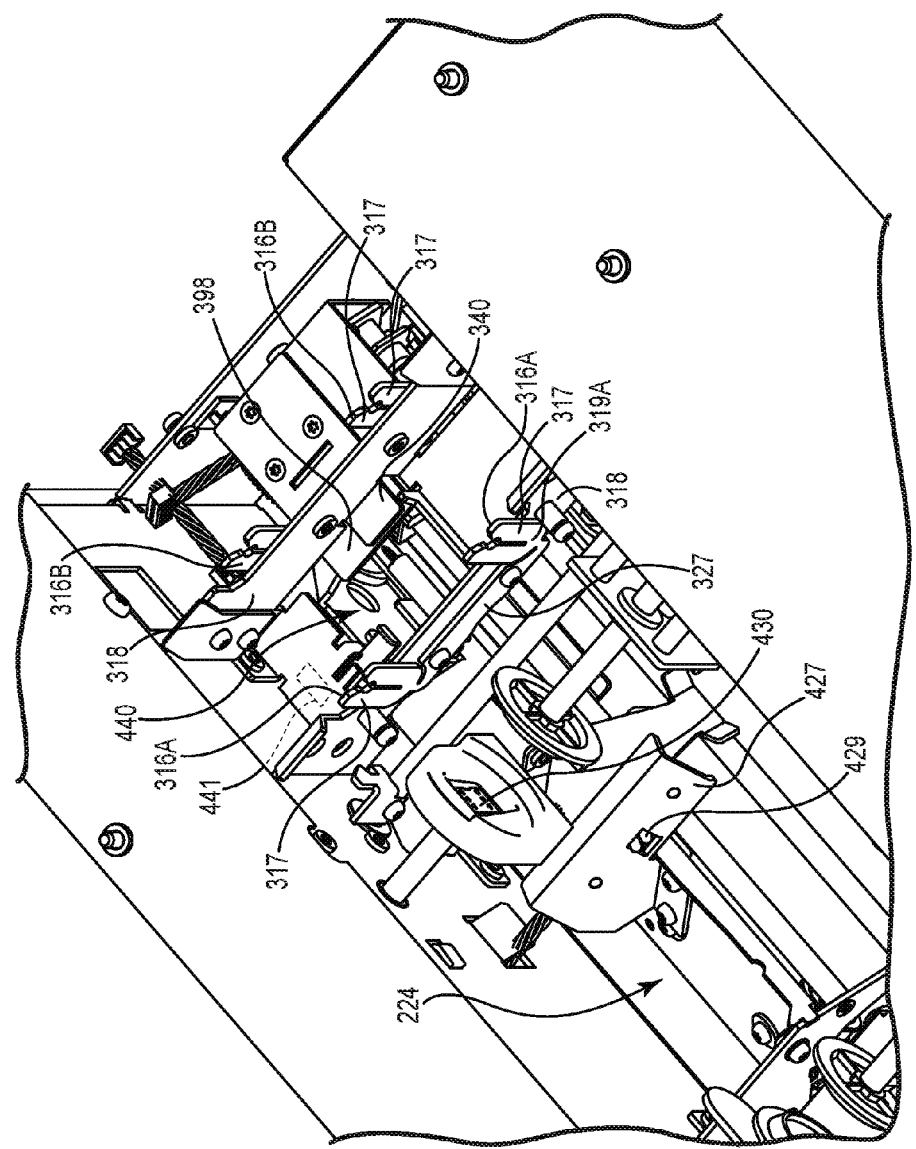
FIG. 27 is an isometric view of the printer shown in FIG. 20, with the lid removed and showing the cassette index assembly and the latches for engaging the hopper.
Figure 28:
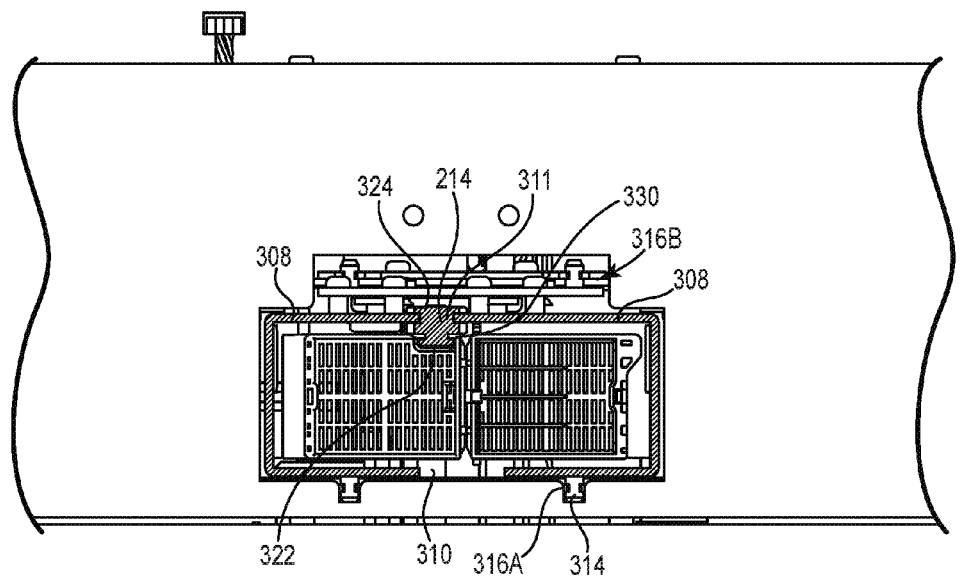
FIG. 28 is a detailed top plan view of the back of the printer shown in FIG. 20, showing the opening in the cover and the hopper and cassette loading rod.
Figure 32:
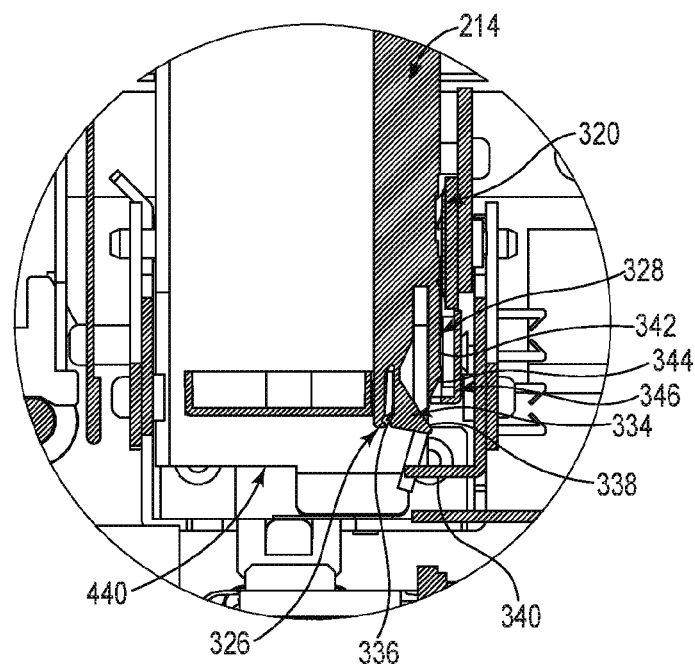
FIG. 32 is a detailed side view of the inside of the printer shown in FIG. 20, showing the loading rod being inserted into the hopper while retaining the cassettes.
Figure 40:
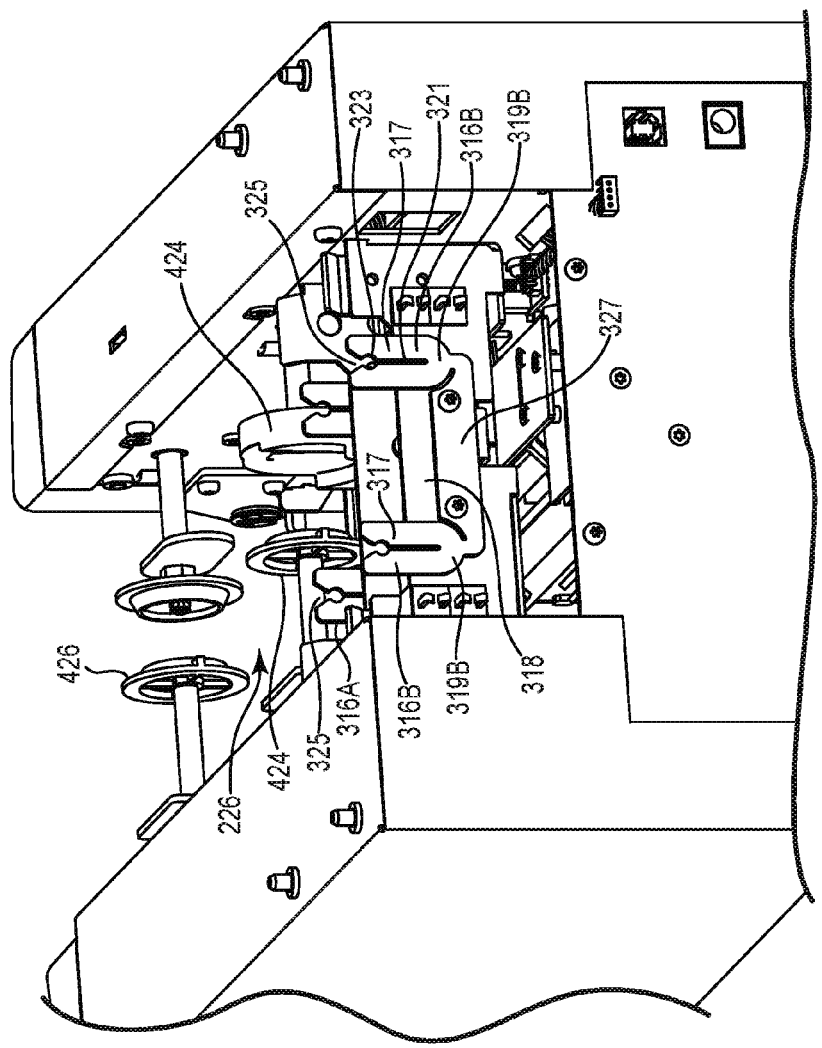
FIG. 40 is an isometric view of the printer shown in FIG. 20, with the lid removed and showing the print ribbon receiving structure.
Figure 41:
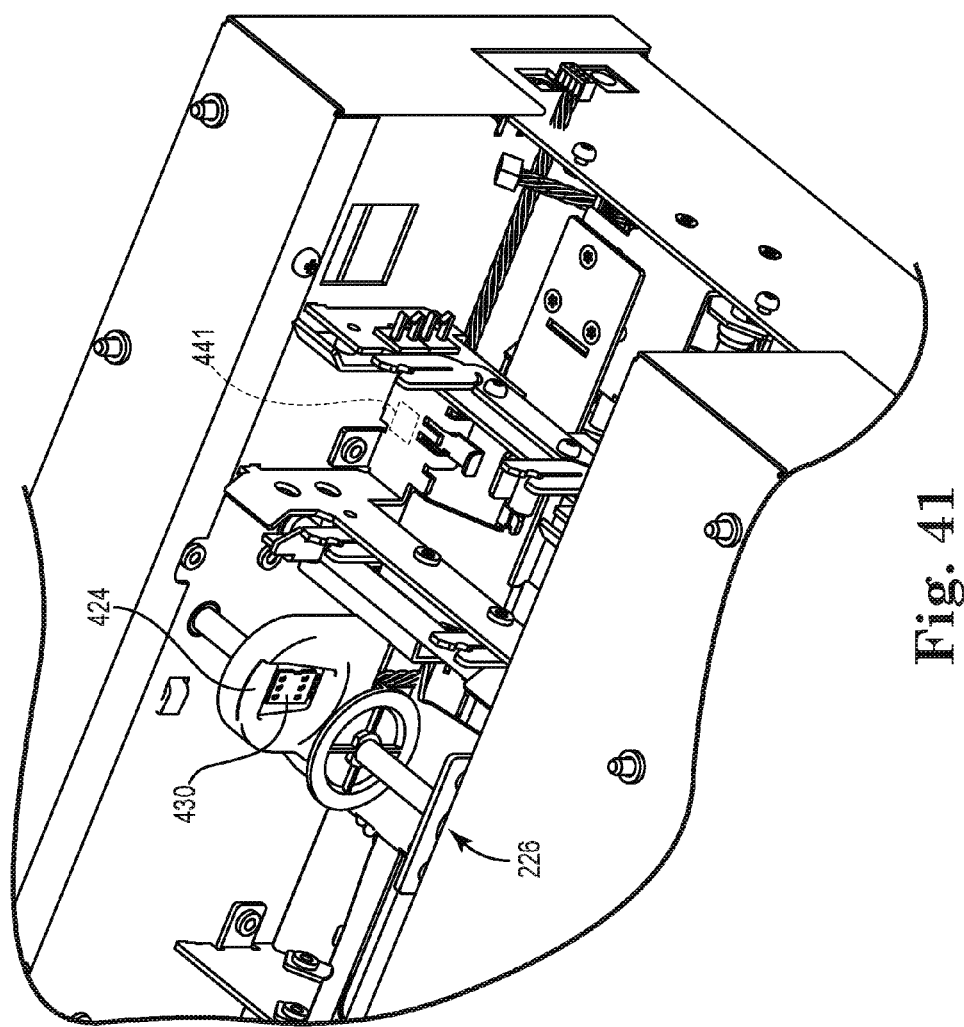
FIG. 41 is an isometric view of the printer shown in FIG. 20, with the lid removed and showing the print ribbon receiving structure.

As perhaps best shown in FIGS. 27 and 40, latches 316A and 316B each have a pair of pinching fingers 317 joined together at neck ends 319A and 319B. The pairs of fingers 317 are separated by slots 321 having expanded pin receiving openings 323. The open ends of the slots 321 also have tapered guide openings 325 that extend into the pin receiving openings 323. In one embodiment, each pair of latches 316A and 316B is formed as a one-piece plastic member with the neck ends 319 of each pair joined to a mount plate 327. When the hopper 212 is inserted into the printer 200, the fingers 317 will flex as the hopper pins 314 are guided into the openings 323 through guide openings 325. The compliant and resilient nature of the latches 316A and 316B cause the fingers 317 to engage the hopper pins 314 in the openings 323. In one embodiment of the invention, the neck ends 319B connecting fingers 317 of latches 316B are wider than the neck ends 319A connecting fingers 317 of latches 316A. Latches 316B are therefor less compliant, and can more accurately locate the end of the hopper 212 adjacent to the picker plate 398 than the end of the hopper engaged by latches 316A. The accuracy and robustness of the cassette picking operations (described below) is thereby enhanced.

Figures 25, 26:
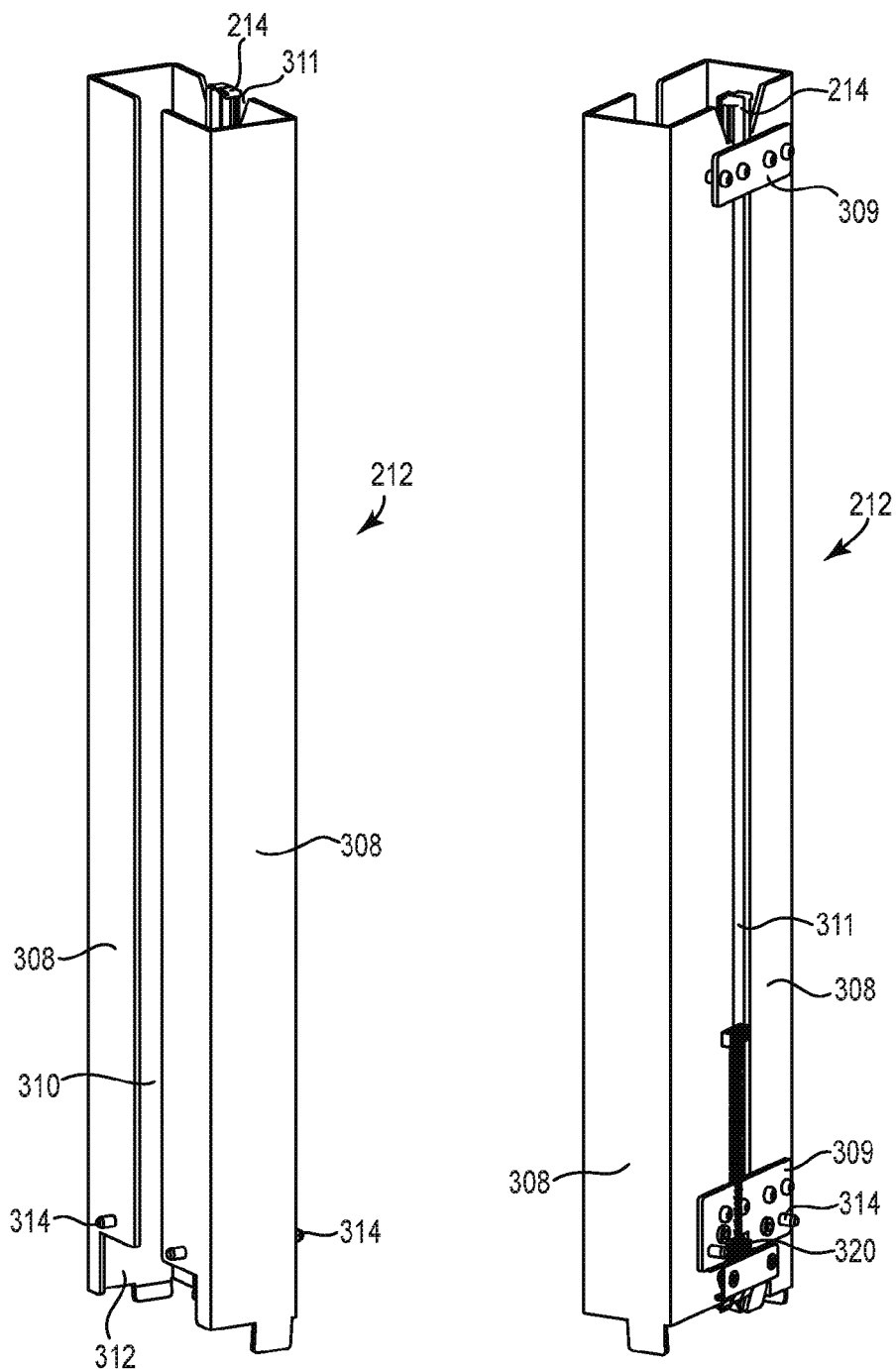
FIG. 25 is an isometric view of the hopper shown in FIG. 20, showing the front side.
FIG. 26 is an isometric view of the hopper shown in FIG. 20, showing the back side.

As perhaps best shown in FIG. 26, an electrical contact 320 is mounted on the back side near the bottom of hopper 212, and as discussed below is configured for electrical coupling to a memory chip 348 on the cassette loading rod 214. Other embodiments of the hopper 212 (not shown) do not include structure for engaging the cassette loading rod. Still other embodiments of the printer 200 (not shown) do not include a hopper 212, or the hopper is fixedly mounted to the printer.

Loading rod 214 and the manner by which it is releasably mounted to the printer 200 can be described with reference to FIGS. 28-33. As shown, the loading rod 214 is an elongated member having a cassette engaging structure in the form of a T-shaped member 322 extending along the length of its front side, a hopper engaging structure in the form of a T-shaped member 324 extending along the length of its back side, a cassette retaining structure 326 on a printer end, and a rod retaining structure 328 on the printer end. The T-shaped member 322 provides a pair of slots 330 that extend along the length of the loading rod 214. The T-shaped member 322 and slots 330 are configured to engage the feed structures on the cassettes and generally constrain movement of the cassettes in a transverse direction with respect to loading rod 214, and to allow a plurality of stacked cassettes to slide long the length of the rod to the cassette retaining structure 326. Similarly, the T-shaped member 324 provides a pair of slots 332 that extend along the length of the loading rod. The loading rod slots 332 are configured to engage the portions of the hopper U-shaped members 308 on opposite sides of the hopper slot 311, enabling the loading rod 214 and cassettes thereon to be slid into the hopper 212, yet be generally constrained from movement in a direction transverse to the hopper. Other embodiments of the loading rod (not shown) do not include a hopper engaging structure. The illustrated embodiment of loading rod 214 includes a memory chip 348. The memory chip 348 is mounted to the loading rod 214 at a position that will enable the memory chip to electrically contact or otherwise be coupled for data transfer with the electrical contact 320 on the hopper 212 when the loading rod is inserted into the printer 200. Other embodiments of the loading rod (not shown) have other cassette engaging structures and/or no hopper engaging structure.

Figure 33:
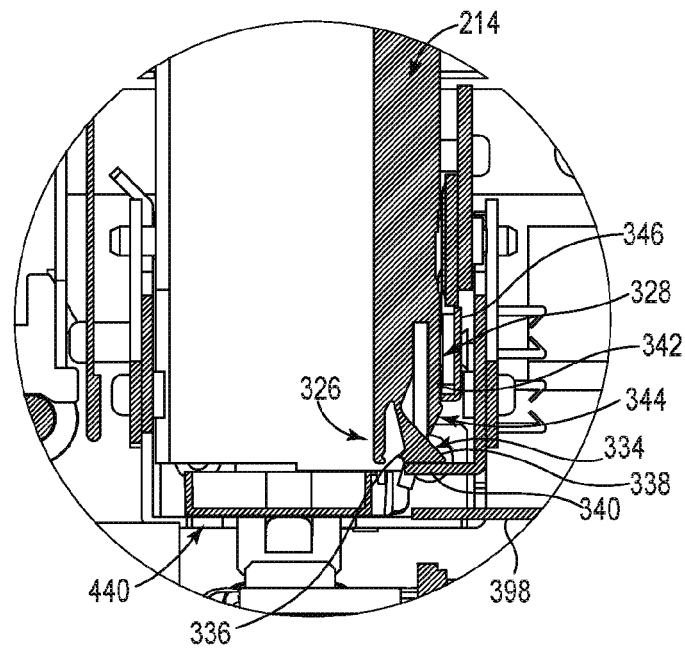
FIG. 33 is a detailed side view of the inside of the printer shown in FIG. 20, showing the loading rod latched into the printer and releasing the cassettes.
Figure 34:
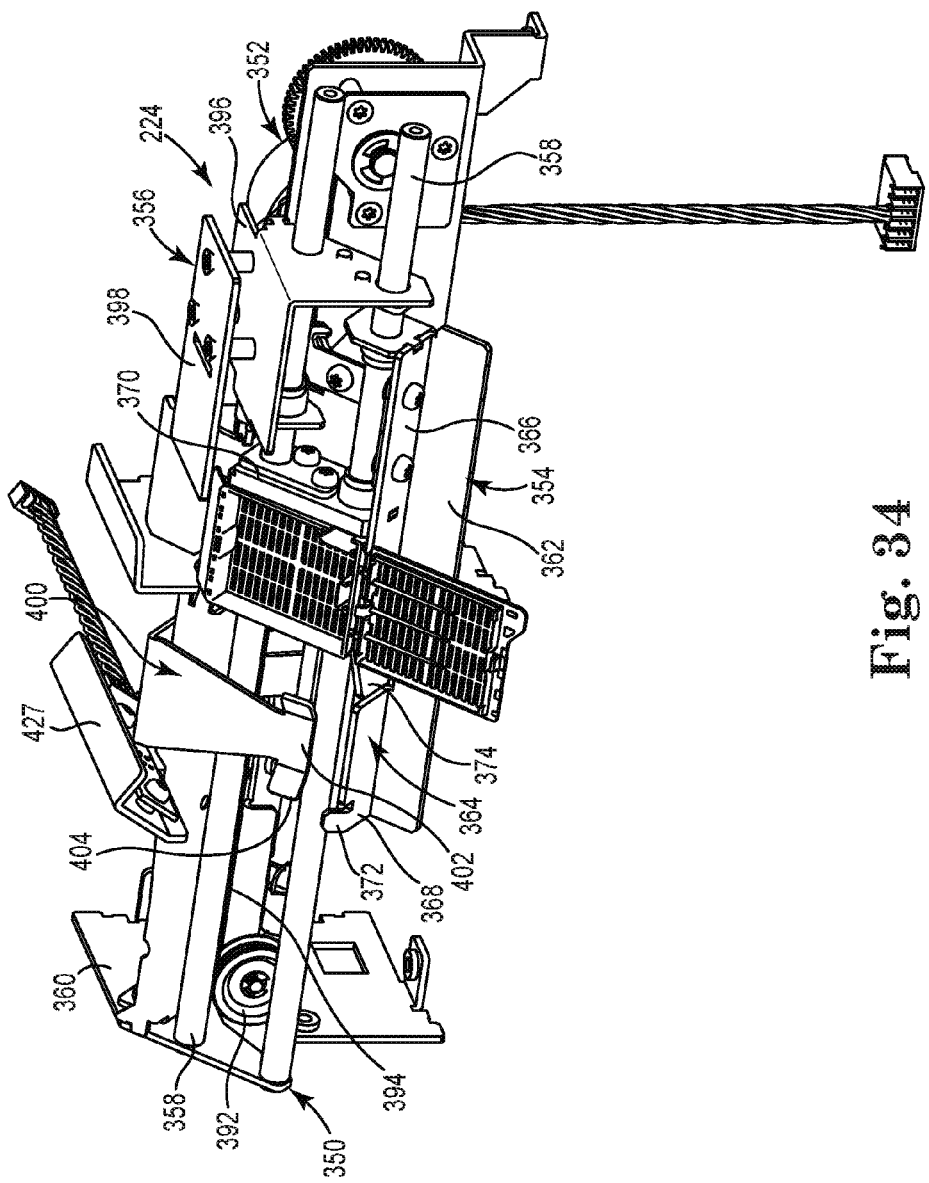
FIG. 34 is an isometric view of the cassette index assembly shown in FIG. 22, with a cassette in a position after picking.
Figure 35:
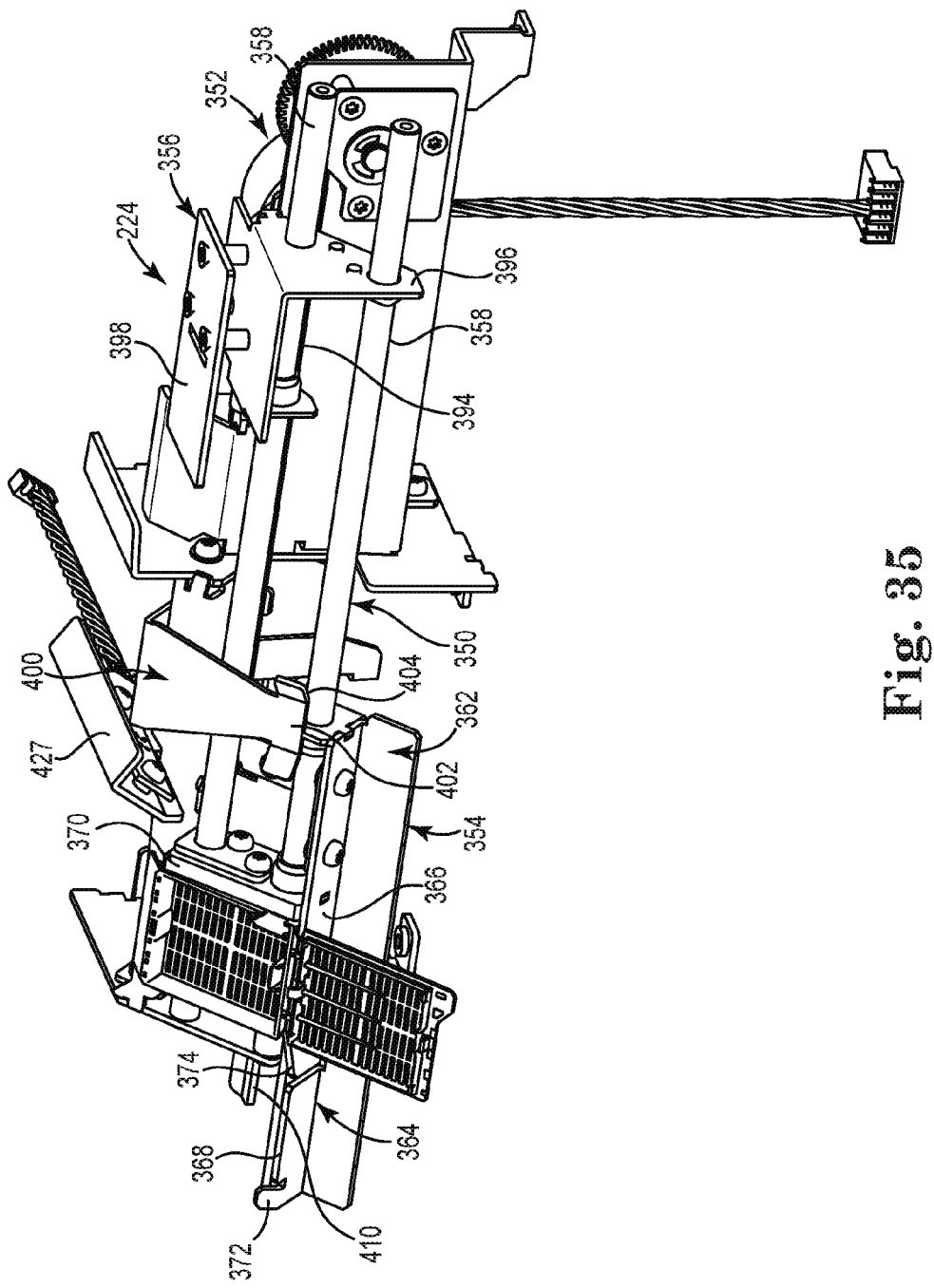
FIG. 35 is an isometric view of the cassette index assembly shown in FIG. 34, with the cassette in a position after printing.
Figure 36:
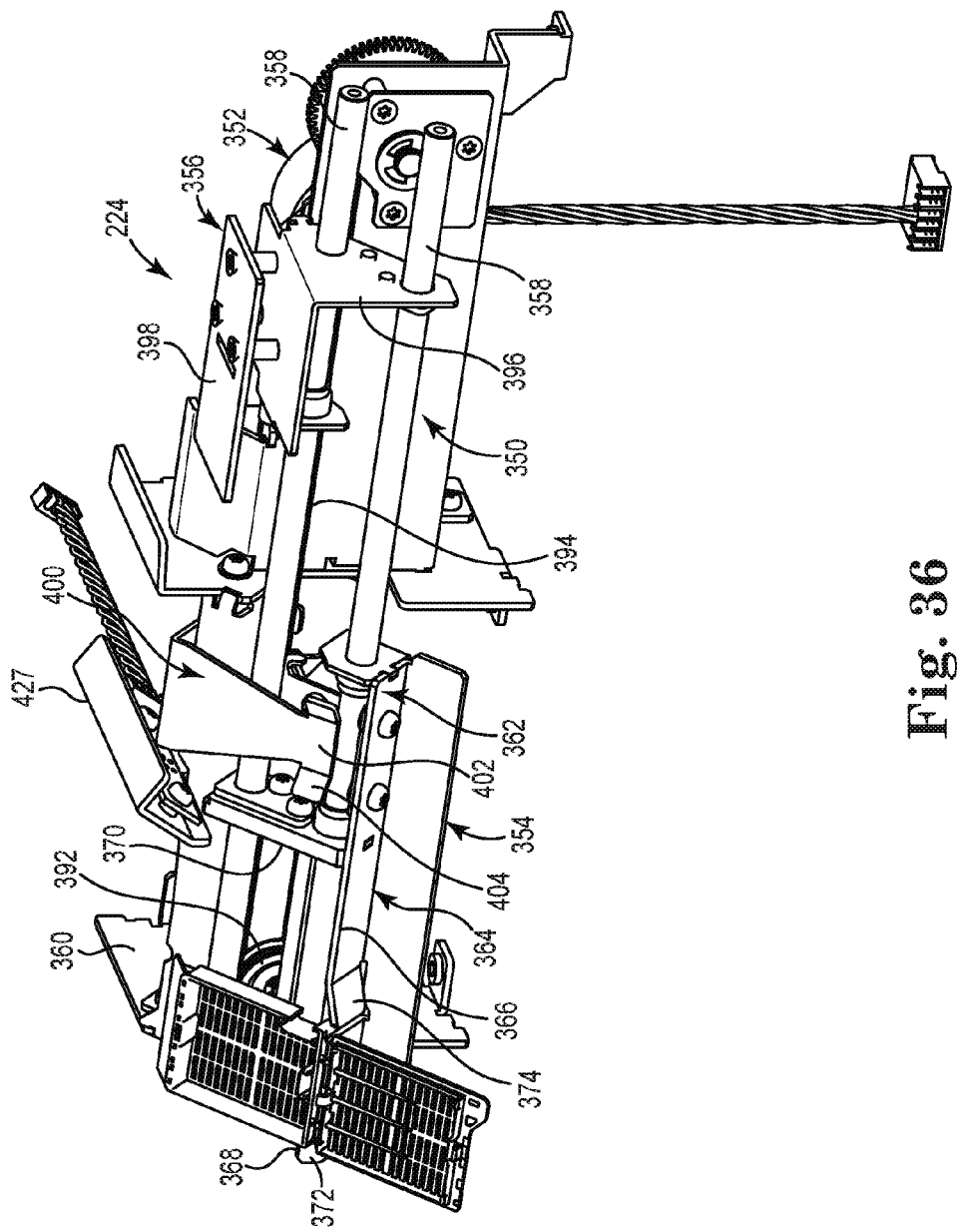
FIG. 36 is an isometric view of the cassette index assembly shown in FIG. 34, with the cassette in a position being reset.

The cassette retaining structure 326 includes a resilient tab 334 having a tooth 336 and an actuation finger 338. When the tab 334 is in its unbiased or neutral position shown in FIGS. 29 and 32, the tooth 336 extends into the slots 330 and under the end-most cassette on the loading rod 214, and prevents the cassettes from sliding off the printer end of the loading rod. Finger 338 functions as a release member. When the loading rod 214 is fully inserted into the printer 200 as shown in FIG. 33, the finger 338 engages a tab 340, and deflects the tab 334 in a direction that retracts the tooth 336 from under the cassettes, allowing the cassettes to slide off the loading rod 214 and onto the cassette index assembly 224. Other embodiments of the loading rod 214 include other cassette retaining structures (not shown), such as for example a tab 334 that is not resilient, and/or an active mechanism for enabling the removal of cassettes from the rod. In yet another embodiment of the invention (not shown), the tab of the cassette retaining structure includes a more flexible hinge, and brackets extend generally transversely from the tab at locations above and below the hinge. A spring is mounted between the brackets to bias the tooth to the cassette retain position at which it extends under the end-most cassette on the loading rod. When this embodiment of the loading rod is inserted into the printer, the finger deflects the tab and tooth against the bias force of the spring.

The rod retaining structure 328 includes a resilient tab 342 and a tapered engaging member 344. When the tab 342 is in its unbiased or neutral position shown in FIG. 32, the member 344 is positioned so that it will engage a bracket 346. As the loading rod 214 is inserted into the printer 200, the member 344 engages the bracket 346 and is deflected with the tab 342. When the loading rod 214 is fully inserted into the printer as shown in FIG. 33, the resilient nature of the tab 342 urges the tab toward its neutral state and causes the member 344 to engage the bracket 346. The rod retaining structure 328 thereby securely retains the loading rod 214 within the printer 200, yet allows the loading rod to be inserted into and removed from the printer by hand without the use of tools. The rod retaining structure 328 also provides a downward (toward the printer) force that causes the deflection of tab 334 and the release of the cassettes on the loading rod 214. Other embodiments of the loading rod (not shown) include a different or no rod retaining structure.

Cassette index assembly 224 and aspects of its operation can be described with reference to FIGS. 22, 27 and 34-38. As shown, the index assembly 224 includes a carriage support 350, a carriage drive 352, a carriage 354 and a picking mechanism 356. Carriage support 350 includes a pair of spaced apart and generally horizontally oriented rods 358 extending between and mounted to brackets such as 360. The rods 358 are positioned to define a support surface that extends at an angle with respect to the y-axis and to support the cassettes at an angle that will position the print panels of the cassettes in the proper printing orientation with respect to the printhead 222 as the cassettes are driven along the printing path past the printhead. In the illustrated embodiment, rods 358 are positioned to define a support surface at an angle of about 45° with respect to printing path, to locate the print panels of the cassettes in a generally horizontal plane corresponding to the horizontally oriented printhead 222 described above (e.g., as shown in FIGS. 21 and 24). Carriage 354 includes a cassette carrier 362 mounted to the rods 358 for reciprocal motion along the printing path that extends in the y-direction. The carrier 362 includes a push bar 370 and a support shelf 364 having a print area 366, reset area 368 and tab 372. Support shelf 364 is a generally elongated member that supports the back walls of the cassettes when the bases of the cassettes are resting on the rods 358. The reset area 368 of the shelf 364 is displaced downwardly in a vertical direction from the print area 366, and is therefore also spaced from the printhead 222 by a greater distance than the print area 366. The vertical distance between the reset area 368 and the print area 366 is also greater than the range of movement of the printhead 222 in the z-direction allowed by the subframe brackets 236 and tabs 240. A sloping transition area 374 joins the print area 366 and the rest area 368 of the shelf 364. An eject finger 410 extends forwardly (i.e. in a downstream direction) from the carrier 362.

Carriage drive 352 includes a stepper motor 376 that is coupled by a drive linkage including gears 388 and 390 to a first pulley (not shown) on a first or input end of the index assembly 224, upstream from the printhead 222. A second pulley 392 is located on a second or output end of the index assembly 224, downstream from the printhead 224. A drive belt 394 extends around pulley 392 and the first pulley, and is coupled to the carriage 354. Motor 376 can thereby drive the carriage 354 on the carriage support 350 in a reciprocal manner along the print path.

Picking mechanism 356 includes a carriage 396 that is mounted to rods 358 for reciprocal motion and a picker plate 398 mounted to the carriage 396. A biasing member such as a spring 359 that extends between tab 361 on the picker mechanism carriage 396 and tab 363 on the carriage support 350 biases the picking mechanism carriage 396 in the first direction toward the output end of the carriage assembly 224. The carriage 396 is driven in the second direction against the bias force of the spring by the carriage 354 as described in greater detail below.

Reset bracket 400 overlays the rods 358 at a reset location that is upstream from the printhead 222. As shown, the reset bracket 400 includes a cassette engaging member 402 having deflection wings 404 on its opposite sides. An end 406 of the member 402 is pivotally mounted to the cassette index assembly 224 so as to enable the cassette engaging member 402 to move in a direction generally perpendicular to the support surface defined by the rods 358. The wings 404 on the reset bracket 400 cause the bracket to deflect upwardly, away from the rods 358, when engaged by a cassette. Motion of the reset bracket 400 is sensed by a reset bracket sensor 408. As described in greater detail below, the reset bracket 400 releasably engages cassettes during reset strokes of the index assembly 224, and causes the cassettes to move between the reset area 368 and the print area 366 of the carrier 362. Sensor 408 senses the presence of cassettes engaged by the reset bracket, and provides signals representative of the sensed cassettes to the control system 434 described in greater detail below.

Figure 42:
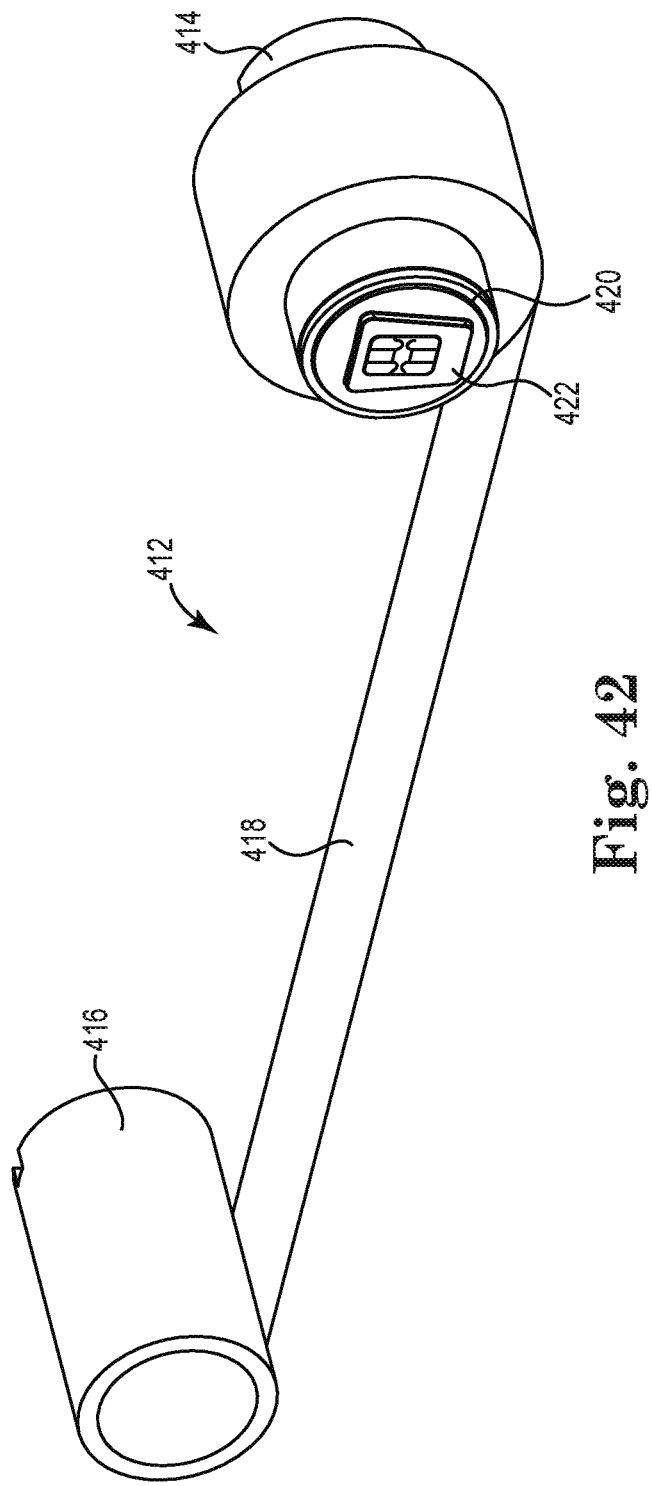
FIG. 42 is an isometric view of a print ribbon that can be used in the printer shown in FIG. 20.
Figure 43:
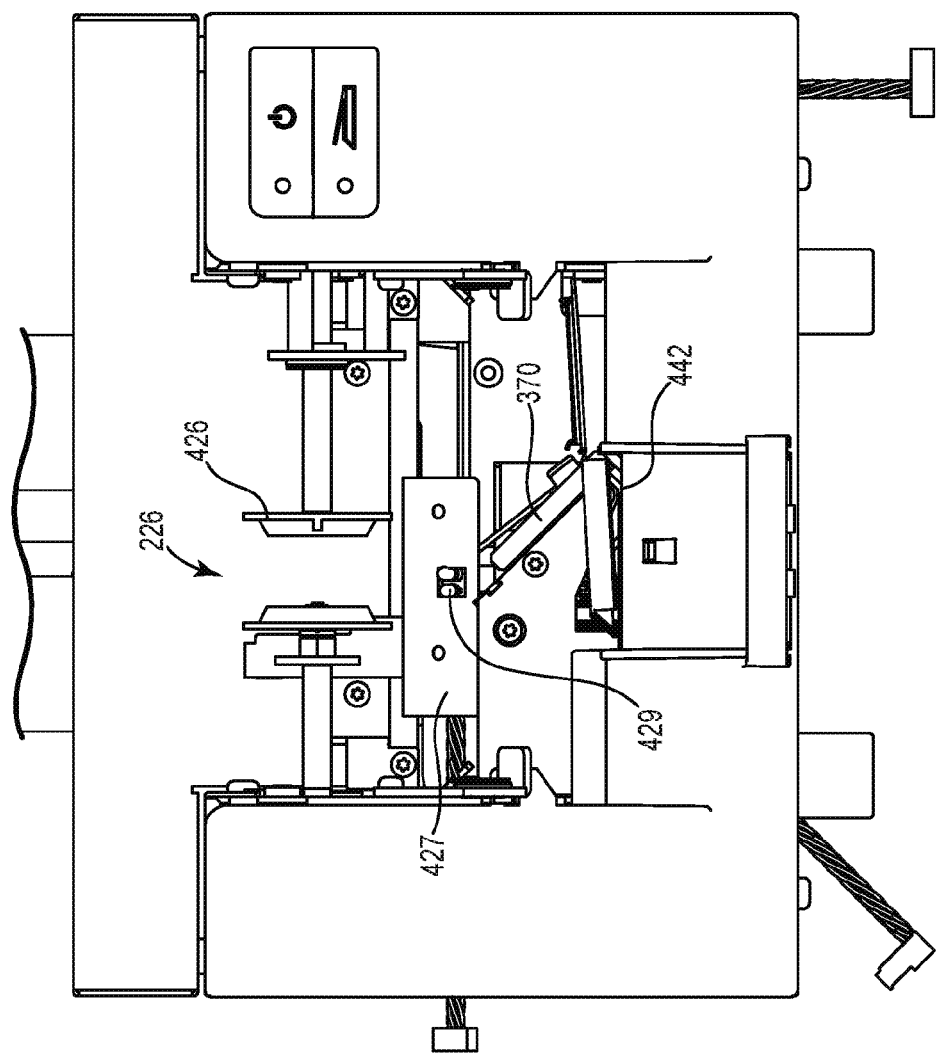
FIG. 43 is a front end plan view of the printer shown in FIG. 20, with the lid removed.

A thermal print ribbon assembly 412 that can be used with printer 200 can be described with reference to FIG. 42. As shown, the print ribbon assembly 412 includes supply spool 414, take-up spool 416, and multi-color thermal ink ribbon 418. The composition of thermal ink ribbons such as 418 is generally known. In one embodiment of the invention the ribbon 418 has a plurality of primary color ink blocks (e.g., yellow, magenta and cyan) and black ink blocks (not separately shown in FIG. 42) spaced in repeating sequences along its length. Rotatably mounted to the take-up spool 414 is a hub 420. A print ribbon memory chip 422 is mounted to the hub 420.

The print ribbon receiving structure 226 for receiving and driving the print ribbon assembly 412 can be described with reference to FIGS. 39-43. As shown, the print ribbon receiving structure 226 includes a pair of supply spool mounts 424 rotatably supported toward the back of the printer 200 and a pair of take-up spool mounts 426 rotatably supported toward the front of the printer. One of both the supply spool mounts 424 and the take-up spool mounts 426 are driven by ribbon drive motors 428 (shown e.g., in FIG. 44) mounted in the enclosure base 204. One of the supply spool mounts 424 includes an electrical contact 430 configured for electrical coupling to the memory chip 422 on the supply spool 414. The print ribbon assembly 412 is loaded onto the print ribbon receiving structure 226 by mounting the supply spool 414 to the supply spool mounts 424, and mounting the take-up spool 416 to the take-up spool mounts 426. The memory chip 422 on the supply spool 414 is electrically coupled to the ribbon supply chip contact 430 when the supply spool is mounted to the supply spool mounts 424. A bracket 427 supporting a pair of ribbon sensor LEDs 429 is mounted to the carriage index assembly 224 (shown, e.g., in FIG. 27). As shown in FIG. 24, after the print ribbon assembly 412 is mounted to the print ribbon receiving structure 226 and the lid 206 is closed, the print ribbon 418 is guided between the supply spool 414 and take-up spool 416, and past the printhead 222, by rollers 290 and 292 and ribbon deflector 288, and passes between the LEDs 429 and the ribbon sensor 306.

Figure 44:
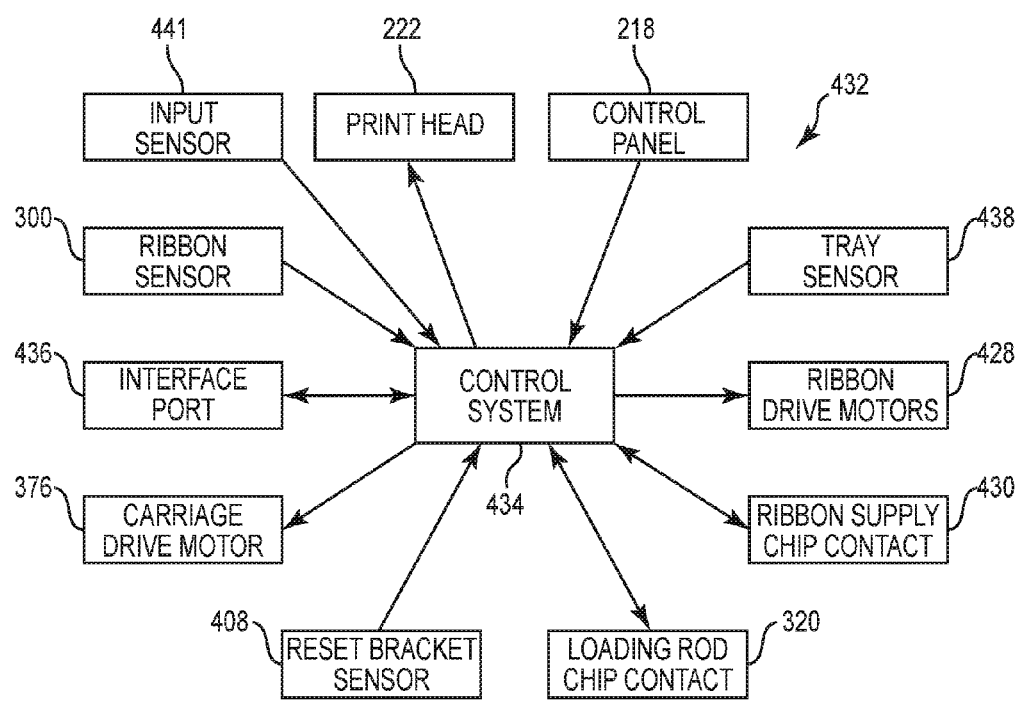
FIG. 44 is a block diagram of the electrical subsystem of the printer shown in FIG. 20.

The electrical subsystem 432 for printer 200 is illustrated in FIG. 44. As shown, the electrical subsystem 432 includes a microprocessor-based control system 434 that is coupled to external devices such as a computer (not shown) through an interface port 436. The control system 434 is also coupled to ribbon sensor 306, printhead 222, control panel 218, tray sensor 438, ribbon drive motors 428, ribbon supply chip contact 430, loading rod chip contact 320, input sensor 441 and reset bracket sensor 408. In one embodiment of the invention, the specimen data is generated on a system such as a PC (not shown). The operator interface and software used to configure the specimen data for print jobs is run on the PC in this embodiment, and the specimen data is received by printer 200 through the interface port 436. For example, the specimen data received at interface port 436 can include color data representative of colors that identify specimen information such as, for example, the type of tissue in the cassette or the tissue source (e.g., clinic location), and the colors that the fields (e.g., color bar, text and bar code) are to be printed. In another embodiment of the invention the control system 434 is programmed to select the colors that the fields are to be printed based on the information received through the interface port (e.g., the control system selects the color yellow based on the knowledge that the tissue is a liver biopsy sample). Other portions of the control system 434 then receive this generated specimen data and control the printer accordingly.

The operation of printer 200 can be described generally with reference to FIGS. 20-44. During setup, the hopper 212 is latched into the enclosure 202 and a loading rod 214 containing a supply of unprinted cassettes is loaded into the hopper and latched into the printer in the manner described above. When the loading rod 214 is inserted, a lower-most cassette on loading rod slides off of the rod onto a staging area 440 (shown e.g., in FIG. 33). The presence of a cassette on the staging area 440 is detected by the input sensor 441 that is coupled to the control system 434. If no cassette is detected on the staging area 440 (e.g., the supply of cassettes is exhausted or the cassettes are jammed on the loading rod 214), control system 434 can respond accordingly (e.g., by providing a responsive display and discontinuing printing operations). In the illustrated embodiment of printer 200, the cassettes are held in a generally horizontal orientation on the staging area 440. Lid 206 is opened during setup to present access to the print ribbon receiving structure 226. After the print ribbon assembly 412 is mounted to the print ribbon receiving structure 226 the lid 206 is closed to locate the print ribbon 418 at the printing position with respect to the printhead 222 in the manner described above. As discussed above, the printer 200 is also connected to a computer or other device (not shown) through the interface port 436 to receive cassette print job information including data representative of the specimen information to be printed on the cassettes during print operations.

Printer 200 is turned on by actuating an ON/OFF switch on the control panel 218. When switched ON, the control system 434 accesses information on the loading rod memory chip 348 through electrical contact 320, and accesses information on the ribbon supply memory chip 422 through the electrical contact 430. Information stored on the loading rod memory chip 348 can include, for example, one or more of cassette type and the number of cassettes remaining on the loading rod 214. Similarly, information stored on the ribbon supply memory chip 422 can include ribbon type, the number of images remaining on the ribbon 418, the production date and batch no. Other or additional types of information can be stored on memory chips 348 and 418. Information on the memory chips 348 and 418 is used to control the operation of printer 200, and can be updated after print operations. For example, if the information on memory chips 348 or 418 indicates that the supply of cassettes or ribbon is exhausted, the control system 434 will not execute a requested print operation. Information stored on memory chips 348 and 422 representative of the number of remaining cassettes and the number of images remaining on the ribbon 418 can be updated following each print operation.

In one embodiment of the invention, the carriage 354 is moved to a fully retracted or home position when the printer is turned on. By this action the carriage 354 urges the picking mechanism 356 to a retracted position against the bias force of spring 359 with the picker plate 398 located behind the cassette on the staging area 440 (shown e.g., in FIG. 33). Print operations are initiated upon the receipt of print job requests. The motor 376 then drives the carriage 354 to the picked position shown in FIG. 34. This movement of the carriage 354 releases the picking mechanism carriage 396 from its retracted position and causes the picker plate 398 to move through a picking stroke during which the picker plate pushes the cassette on the staging area 440 off the staging area and in the first direction toward the carrier 362 of the cassette index assembly 224. This picking stroke causes the base of the cassette to fall under the force of gravity onto the print area 366 of the shelf 364, with the bottom wall of the base resting on the support surface formed by the rods 358 and the back wall of the base resting on the shelf (shown e.g., in FIG. 34). The print zone on the cassette is thereby positioned to pass by the printhead 222 during the print operation at a printing position (i.e., with the print zone at a position with respect to the printhead that enables printing onto the print zone). Another cassette will slide off the loading rod 214 and drop onto the picker plate 398 during the picking stroke. During the remaining portions of the print operation described below, the picking mechanism 356 remains in the picked position with the picker plate 398 supporting a cassette above the staging area 440.

After picking, the cassette carriage 354 is driven from the picked position through a printing stroke. During the printing stroke the push bar 370 pushes the cassette in the first or downstream direction, while the cassette is located on the print area 366 of the shelf 364, past the reset bracket 400 and past the printhead 222 to a print stroke end position (shown e.g., in FIG. 35). As the cassette is driven past the reset bracket 400 the deflection wings 404 cause the bracket to be lifted up and to ride over the cassette, and thereby not interfere with the motion of the cassette during the printing stroke. In connection with the printing stroke the control system 434 actuates the ribbon drive motors 428 to position an ink panel of the selected color of the print ribbon 418 over the printhead 222 before the cassette is driven past the printhead. Signals received from ribbon sensor 306 are used by the control system 434 to assure that the selected color panel of the ink ribbon 418 is positioned over the printhead 222. During the printing stroke the control system 434 actuates the printhead 222 as a function of the specimen data to heat and transfer ink from the print ribbon 418 and to print the specimen information onto the print zone on the cassette.

The specimen information printed on the cassette can be the same as or similar to that printed by slide printer 10 and described above. For example, a color bar can be printed at a first location, a bar code can be printed at a second location, and text can be printed at a third location. These information fields can be printed in any of a wide variety of colors using the ink available on the print ribbon 418. For example, the selected color(s) can be any one or more of the colors of the primary and black ink panels, or colors available from any combination of the colors of the primary and black ink panels. The colors can, but need not be, selected to represent sample information such as the tissue type or the source of the tissue. A bar code or other information field intended for machine-reading can, for example, be printed in black ink to maximize its contrast with the print zone background.

If the requested print operation includes multiple color printing (e.g., a magenta color bar and/or magenta text and a black bar code, or a color bar having a color formed by a combination of two or more primary and/or back colors), the control system 434 actuates the ribbon drive motors 428 to position the appropriate color ink panel of the print ribbon 418 adjacent to the printhead 222, and drives the carriage through a reset stroke and another printing stroke. During the reset stroke the carriage 354 is driven in the second or upstream direction. As the carriage 354 is driven in the second direction, the side wall of the cassette on the front end near the print panel (i.e., the upstream side) will engage the back of the printhead 222 (i.e., the downstream end of the printhead) and stop the motion of the cassette with respect to the printhead. With continued motion of the carriage 354 the cassette will then slide on the shelf 364 from the print area 366, across the transition area 374 and over the reset area 368. Because the reset area 368 is vertically displaced from the print area 366, the cassette will drop down onto the reset area of the shelf 364 under the force of gravity (shown e.g., in FIG. 36). Other embodiments of the invention (not shown) have other structures such as active mechanisms for moving cassettes from the print area to the reset area. As described above, the printhead 222 and carriage 354 are configured in such a manner that when the cassette is on the reset area 368, the cassette is below the printhead to space the print zone of the cassette from the printing position, and provide clearance between the cassette print zone and the printhead during the reset strokes. With continued motion in the second direction during the reset stroke the carriage 354 causes the tab 372 on the shelf 364 to engage the cassette, and to drive the cassette in the second direction back under and past the printhead 222.

Figure 37:
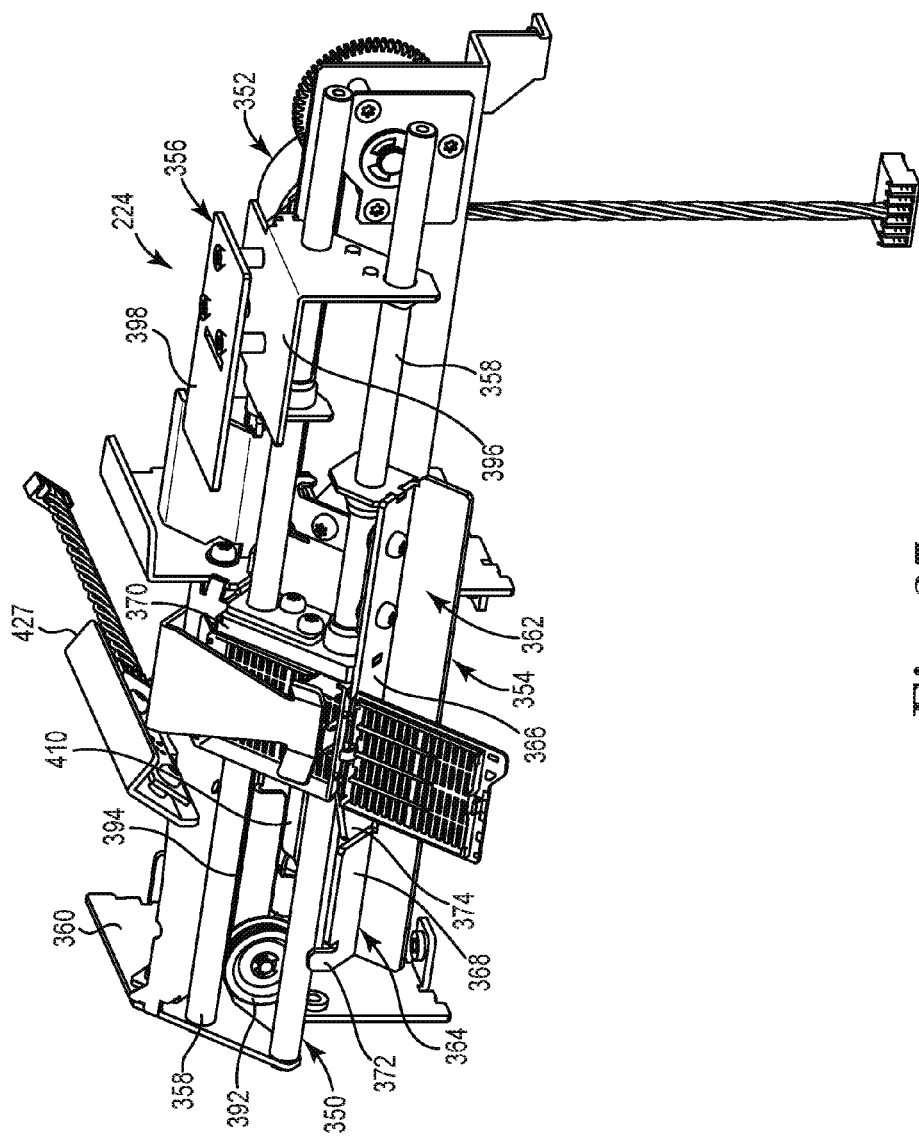
FIG. 37 is an isometric view of the cassette index assembly shown in FIG. 34, with the cassette in a position after being reset.
Figure 38:
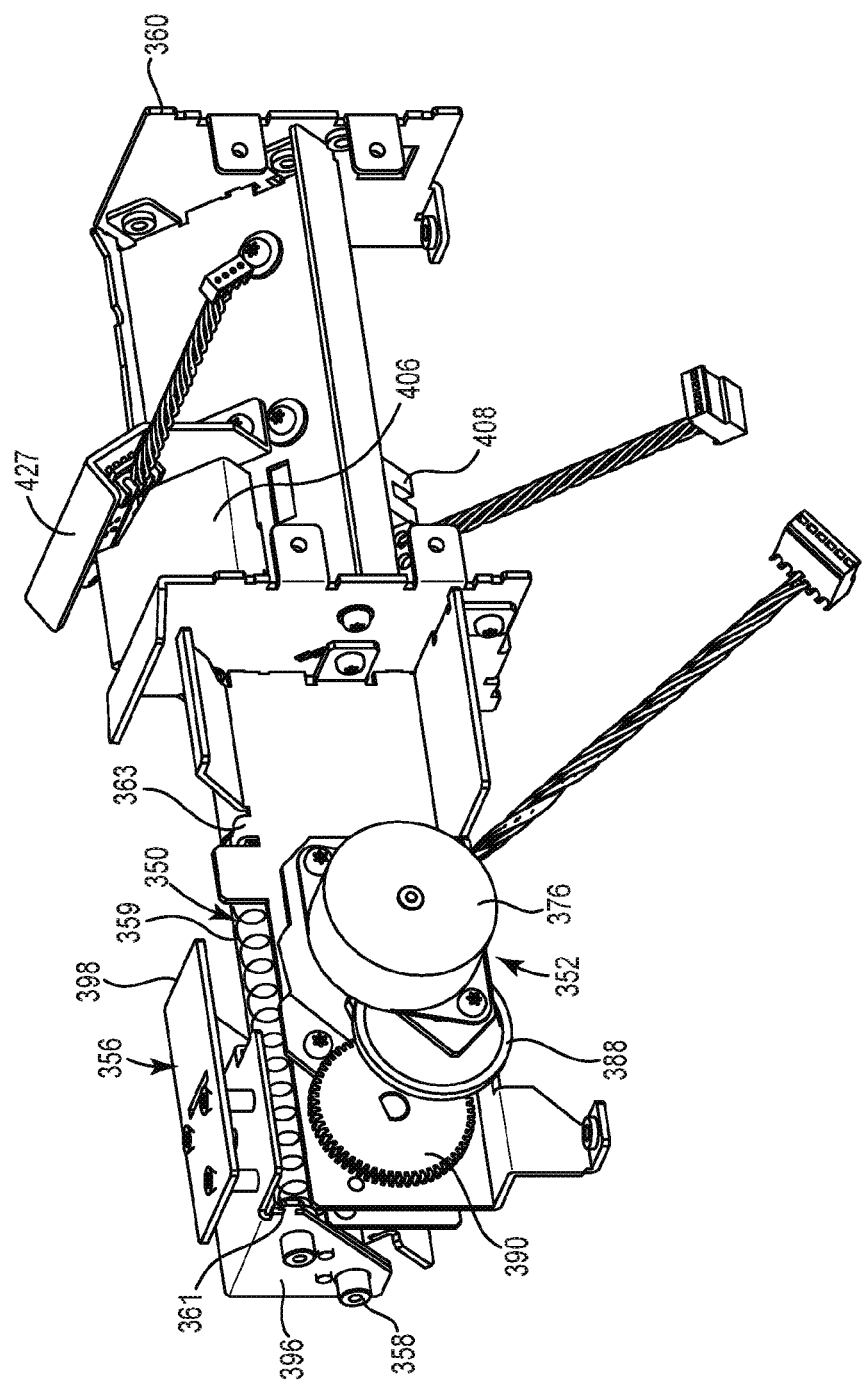
FIG. 38 is an isometric view of the cassette index assembly shown in FIG. 34, showing a side opposite the side shown in FIG. 34.
Figure 39:
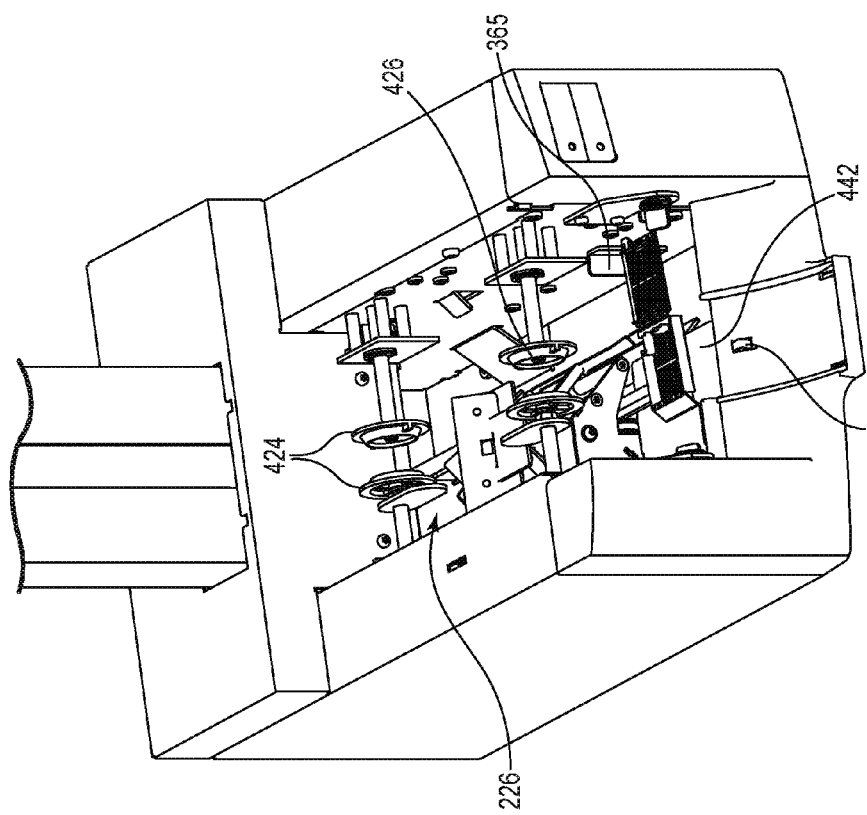
FIG. 39 is an isometric view of the printer shown in FIG. 20, with the lid removed and showing the cassette index assembly and print ribbon receiving structure.

During this portion of the reset stroke the cassette will engage the downstream deflection wing 404 on the reset bracket 400, and deflect the reset bracket upwardly over the cassette. At the end of this portion of the reset stroke the cassette is located under the reset bracket 400, with the reset bracket resting on the cassette and the cassette on the reset area 368 of the shelf and the push bar 370 spaced from the upstream side wall of the cassette. During a subsequent portion of the reset stroke the carriage 354 is again driven in the first direction. The force of the reset bracket 400 on the cassette is sufficient that during this motion of the carriage 354 the cassette will remain positioned under the reset bracket, and slide from the reset area 368 up the transition area 374 and onto the print area 366 (i.e., as shown in FIG. 37). A printing stroke of the type described above is then repeated to print specimen information in the second color. The control system 434 can actuate the ribbon drive motors 428 to advance the print ribbon 418, and to drive the carriage 354 in reciprocal manner through additional reset and printing strokes, to print specimen information in third or third and fourth colors if specified by the requested print operation. Other embodiments of the invention (not shown) include other mechanisms for providing clearance by moving the cassettes around the generally fixed position printhead between different color print strokes.

Following the completion of the final printing stroke the control system 434 drives the carriage 354 through an eject stroke. During a first portion of the eject stroke the carriage 354 is driven in the forward direction to such an extent that the printed cassette is pushed off of the rods 358. At this position the cassette rotates on the carriage shelf 364, and the base of the cassette drops onto the eject finger 410 (shown e.g., in FIG. 22) and the lid of the cassette rises to a position downstream of a sideplate tab 365 (shown e.g., in FIG. 39). During a second portion of the eject stroke the carriage is moved in the second direction to urge the upstream side wall of the cassette into engagement with the carriage bracket 360, to urge the upstream side wall of the lid into engagement with the sideplate tab 365, and to withdraw the eject finger 410 from under the cassette. The action of this portion of the eject stroke causes the base of the printed cassette to drop off of the eject finger 410 and onto a ledge 442 between the carriage 354 and the slide 216 (shown e.g., in FIG. 43), with the upstream end of the cassette base still resting on the carriage 354. The carriage 354 is then driven in the forward direction through another portion of the eject stroke to engage the eject finger 410 with the upstream side wall of the printed cassette, and to push the cassette from the ledge 442 over the slide 216. The printed cassette will then move down the slide 216 and exit the printer 200. Control system 434 will discontinue print operations if tray sensor 438 is actuated, indicating that the slide 216 is full of printed cassettes. Following the completion of the eject stroke the carriage 354 is driven back to its home position if another cassette print job is pending. As the carriage 354 is driven back to its home position it urges picking mechanism 356 back to its retracted position which causes the picker plate 398 to be withdrawn from under the next cassette, and causes the cassette to drop onto the staging area 440.

Figure 45:
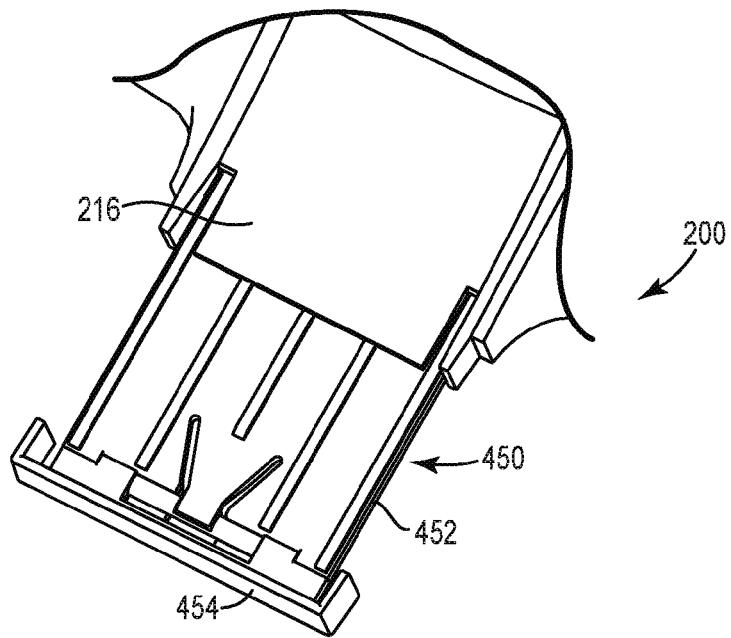
FIG. 45 is a detailed isometric view of an output tray and stop in accordance with another embodiment of the printer shown in FIG. 20.
Figure 46:
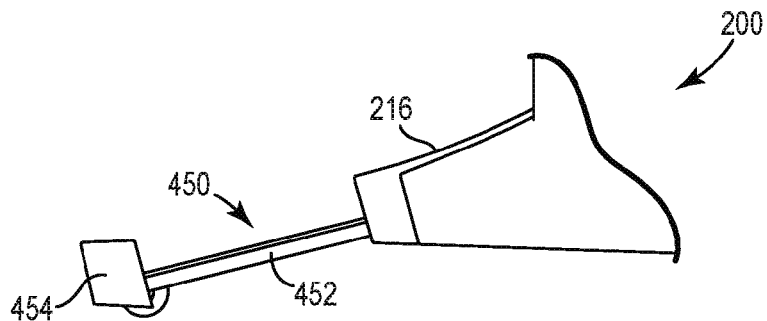
FIGS. 46 and 47 are side views of the output tray and stop shown in FIG. 45, with the stop shown in up and down positions, respectively.
Figure 47:
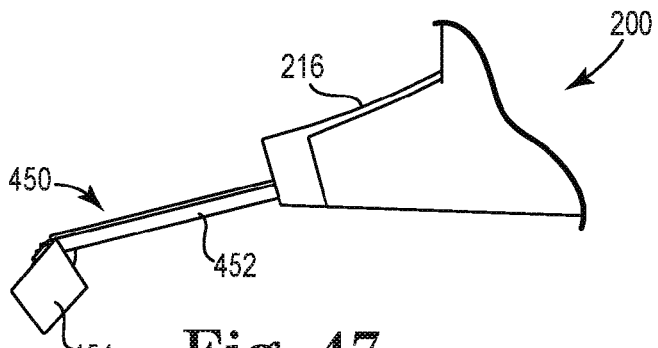
Figure 50:
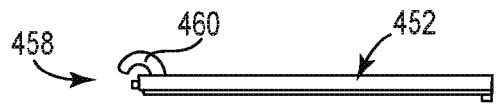
FIGS. 48-51 are top plan, end plan, side plan and isometric views, respectively of the base of the output tray shown in FIGS. 45-47.
Figures 48, 49:
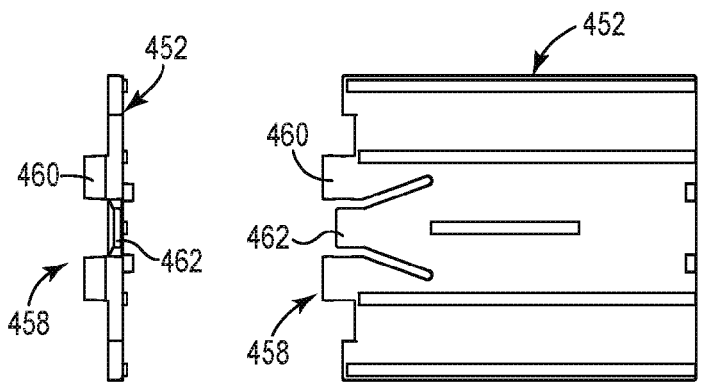
Figure 51:
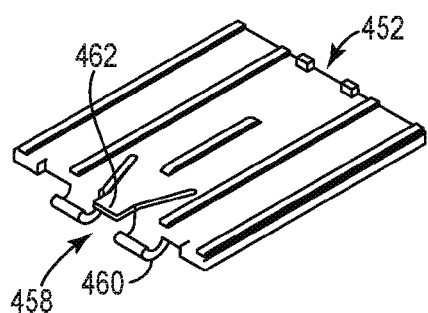

An output tray 450 that can be included in some embodiments of the printer 200 is illustrated in FIGS. 45-47. In the illustrated embodiment, the output tray 450 includes a base 452 that is mounted to the base 204 of the enclosure 206 below the slide 216, and a stop 454 on the end of the base 452. The base 452 is slidably mounted with respect to the slide 216, and is shown in the extended position in FIGS. 45-47. The base 452 can also be moved to a retracted position (not shown) with the stop 454 located at the bottom of slide 216. The stop 454 can be moved by an operator without the use of tools between an up position shown in FIG. 46 and a down position shown in FIG. 47. When in the up position the stop 454 will retain printed cassettes on the base 452 and/or slide 216. When the stop 454 is in the down position cassettes will be able to slide off of the base 452 and/or slide 216.

A pivotal latch structure that includes a shaft 456 on the stop 454 and a shaft receiving structure 458 on the base 452 can be described with reference to FIGS. 48-53. As shown, the shaft receiving structure 458 includes one or more hooks 460 and one or more tongues 462 extending from the distal end of the base 452 at transversely spaced positions. The illustrated embodiment includes a pair of hooks 460 and a single tongue 462 between the hooks. Other embodiments (not shown) can include other arrangements of hooks 460 and tongues 462. The hooks 460 and tongue 462 define a rotational axis and are configured to receive the shaft 456 on the stop 454. The shaft 456 includes cylindrical sections 464 that rotatably mate with the hooks 460 and flat surfaces 466 at locations corresponding to the location of the tongue 462. When the stop 454 is in the up position, the tongue 462 is engaged with one of the flat surfaces 466 to releasably retain or latch the stop in the up position. Similarly, the tongue 462 can engage another of the flat surfaces 466 to releasably latch the stop 452 in the down position.

Although the present invention has been described with reference to preferred embodiments, those skilled in the art will recognize that changes can be made without departing from the spirit and scope of the invention. For example, some embodiments of the claimed invention can be implemented in ink jet, laser or other printers in addition to the thermal printers described herein.

The invention claimed is:

1. A unitary molded polymer histological specimen cassette, comprising:
    a base defining a compartment;
    a panel extending from the base and having a print-receptive front surface, a rear surface and a first thickness, wherein the panel has a length, a width that is less than the length, and a lengthwise edge connected to and integrally molded with the base; and
    at least four spaced apart support walls extending between and integrally molded with the base and the rear surface of the panel to support the panel with respect to the base, wherein the plurality of support walls includes a sufficient number of support walls at spaced-apart positions to provide the panel with sufficient rigidity to enable printing on the print-receptive surface, and wherein all of the plurality of support walls have a substantially equal second thickness that is less than the first thickness of the panel and wherein the second thickness is a thickness with respect to the first thickness that causes the panel to be sufficiently flat and smooth to enable printing on the print-receptive surface; and
    wherein the lengthwise edge of the panel and the plurality of support walls comprise the only connections between the panel and the base, and wherein the print-receptive surface is substantially free from molding cooling-induced indents at intersections of the support walls and panel.

2. The molded polymer specimen cassette of claim 1 wherein the print-receptive surface is free from post-molding finishing.

3. The molded polymer specimen cassette of claim 1 wherein the support walls have a second thickness between about 32% and 60% of the first thickness of the panel.

4. The molded polymer specimen cassette of claim 3 wherein the support walls have thicknesses between about 0.013 and 0.024 inches.

5. The molded polymer specimen cassette of claim 1 and further including a feed structure slot on the base.

6. The histological specimen cassette of claim 1 and further comprising:
a lid;
a hinge connecting the lid to the base and enabling the lid to move between an open position and a closed position with respect to the base; and
wherein the lid and base are configured to form a fulcrum and apply sufficient tension to the hinge to fracture the hinge when the lid is moved from the open position to the closed position.

7. The specimen cassette of claim 6 wherein:
the hinge has a length;
locations that the hinge connects to the base and the lid are separated by a first distance when the lid is in the closed position; and
the length of the hinge is less than the first distance.

8. The specimen cassette of claim 7 wherein:
the hinge is thinner than the base at the location that the hinge connects to the base; and
the hinge is thinner than the lid at the location that the hinge connects to the lid.

9. The specimen cassette of claim 6 wherein:
the base includes a bottom wall and a hinge end side wall portion having an upper edge;
the lid includes a hinge end portion having an underside surface portion;
the hinge connects the hinge end portion of the lid to the hinge end side wall portion of the base; and
the upper edge of the hinge end side wall portion of the base and the underside surface portion of the hinge end portion of the lid cooperate to form the fulcrum when the lid is moved from the open position to the closed position.

10. The specimen cassette of claim 9 wherein:
the hinge has a length;
locations that the hinge connects to the hinge end side wall portion of the base and the hinge end portion of the lid are separated by a first distance when the lid is in the closed position; and
the length of the hinge is less than the first distance.

11. The specimen cassette of claim 10 wherein:
the hinge is thinner than the base at the location that the hinge connects to the base; and
the hinge is thinner than the lid at the location that the hinge connects to the lid.

12. The specimen cassette of claim 9 and further including a first guide structure on the hinge end side wall portion of the base and the hinge end portion of the lid, wherein the first guide structure is disengaged when the lid is in the open position, engages before the hinge fractures when the lid is moved to the closed position, and prevents the hinge end portion of the lid from sliding toward the compartment with respect to the base when engaged.

13. The specimen cassette of claim 12 wherein the first guide structure includes:
a guide projection on one of the hinge end portion of the lid and the hinge end side wall portion of the base; and
a recess on the other of the hinge end portion of the lid and the hinge end side wall portion of the base.

14. The specimen cassette of claim 12 wherein:
the hinge end side wall portion of the base includes a flange extending in a direction opposite the compartment;
the hinge end portion of the lid includes a flange; and
the hinge connects the flange of the hinge end side wall portion of the base to the flange of the hinge end portion of the lid.

15. The specimen cassette of claim 14 wherein the first guide structure is on the flanges of the hinge end side wall portion of the base and the hinge end portion of the lid.

16. The specimen cassette of claim 12 wherein:
the base further includes a front end side wall portion opposite the compartment from the hinge end side wall portion;
the lid further includes a front end portion; and
the cassette further includes a latch structure on the front end side wall portion of the base and the front end portion of the lid, to releasably latch the lid to the base when the lid is in the closed position.

17. The specimen cassette of claim 16 and further including a second guide structure on the hinge end side wall portion of the base and the hinge end portion of the lid, wherein the second guide structure is disengaged when the lid is in the open position, engages before the lid is in the closed position, and releasably holds the hinge end portion of the lid to the hinge end side wall portion of the base when the hinge is fractured.

18. The specimen cassette of claim 9 wherein:
the hinge end side wall portion of the base includes a flange extending from the upper edge;
the hinge end portion of the lid includes a flange; and
the hinge connects the flange of the hinge end side wall portion of the base to the flange of the hinge end portion of the lid.

19. The specimen cassette of claim 6 and further including a feed structure slot on the base.

20. The molded polymer specimen cassette of claim 6 and further including a latch structure to releasably latch the lid to a front end wall of the base when the lid is in the closed position.

21. The molded polymer specimen cassette of claim 20 and further including a guide structure comprising:
a guide finger on one of a rear end portion of the lid and a rear end wall of the base; and
a recess on the other of the rear end portion of the lid and the rear end wall of the base, wherein the guide finger is disengaged from the recess when the lid is in the open position, engages the recess before the lid is in the closed position, and releasably holds the rear end portion of the lid to the base when the hinge is fractured.

* * * * *